(12) United States Patent
Deo

(10) Patent No.: US 11,152,232 B2
(45) Date of Patent: *Oct. 19, 2021

(54) FREQUENCY AND PHASE CONTROLLED TRANSDUCERS AND SENSING

(71) Applicant: Anand Deo, Mendota Heights, MN (US)

(72) Inventor: Anand Deo, Mendota Heights, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/780,554

(22) Filed: Feb. 3, 2020

(65) Prior Publication Data

US 2020/0176283 A1 Jun. 4, 2020

Related U.S. Application Data

(63) Continuation-in-part of application No. 16/666,773, filed on Oct. 29, 2019, and a continuation-in-part of
(Continued)

(51) Int. Cl.
*H01L 21/67* (2006.01)
*H05B 6/50* (2006.01)
(Continued)

(52) U.S. Cl.
CPC .......... *H01L 21/67103* (2013.01); *A61F 7/12* (2013.01); *H01L 21/324* (2013.01);
(Continued)

(58) Field of Classification Search
CPC .............................................. H01L 21/67103
(Continued)

(56) References Cited

U.S. PATENT DOCUMENTS 3,780,255 A 12/1973 Boom
4,338,575 A 7/1982 Hartemann
(Continued)

FOREIGN PATENT DOCUMENTS

CA 2993930 A1 2/2017
CN 106267534 A 1/2017
(Continued)

OTHER PUBLICATIONS

U.S. Appl. No. 15/165,096 U.S. Pat. No. 9,536,758, filed May 26, 2016, Time-Varying Frequency Powered Semiconductor Substrate Heat Source.
(Continued)

*Primary Examiner* — Joseph Chang
(74) *Attorney, Agent, or Firm* — Schwegman Lundberg & Woessner, P.A.

(57) ABSTRACT

Localized heating can use a fixed-frequency planar transmission line resonators arranged along a main-line, selected by tuning an electromagnetic input signal frequency applied to the main line for depositing heat in an adjacent active substrate. More generally, adjusting input signal frequency can be used to selectively address and energize an electromagnetic-to-heat, an electromagnetic-to-vibration, or other transducer to controllably direct energy toward a desired transducer load. Resonators or other electromagnetically energized transducers can be arranged to electromagnetically interfere, such that specifying or adjusting a relative phase of applied electrical signals can be used to specify or adjust the energy directed toward a desired transducer load. Temperature sensing can characterize a material in a target region near the transducer. A cold-hot-cold temperature profile can better manage temperature and avoid overheating a dielectric material such as the active substrate material.

29 Claims, 18 Drawing Sheets

Related U.S. Application Data application No. 16/502,989, filed on Jul. 3, 2019, now Pat. No. 10,553,462, which is a continuation of application No. 16/027,139, filed on Jul. 3, 2018, now Pat. No. 10,515,831, said application No. 16/666,773 is a continuation of application No. 16/027,139, filed on Jul. 3, 2018, now Pat. No. 10,515,831, said application No. 16/027,139 is a continuation-in-part of application No. PCT/US2016/069490, filed on Dec. 30, 2016, which is a continuation of application No. 15/165,096, filed on May 26, 2016, now Pat. No. 9,536,758.

(60) Provisional application No. 62/693,881, filed on Jul. 3, 2018, provisional application No. 62/530,035, filed on Jul. 7, 2017.

(51) Int. Cl.
  *A61F 7/12* (2006.01)
  *H01L 21/324* (2006.01)
  *H05B 1/02* (2006.01)

(52) U.S. Cl.
  CPC ....... *H01L 21/67248* (2013.01); *H05B 1/023* (2013.01); *H05B 6/50* (2013.01)

(58) Field of Classification Search
  USPC ...................................................... 438/795
  See application file for complete search history.

(56) References Cited

U.S. PATENT DOCUMENTS

| | | | |
|---|---|---|---|
| 4,945,912 A | 8/1990 | Langberg | |
| 5,037,395 A | 8/1991 | Spencer | |
| 5,057,105 A | 10/1991 | Malone et al. | |
| 5,191,883 A | 3/1993 | Lennox et al. | |
| 5,257,635 A | 11/1993 | Langberg | |
| 5,260,020 A | 11/1993 | Wilk et al. | |
| 5,290,490 A | 3/1994 | Nied et al. | |
| 5,498,261 A | 3/1996 | Strul | |
| 5,810,802 A | 9/1998 | Panescu et al. | |
| 5,891,182 A | 4/1999 | Fleming | |
| 6,157,804 A | 12/2000 | Richmond et al. | |
| 6,387,052 B1 | 5/2002 | Quinn et al. | |
| 6,443,547 B1 | 9/2002 | Takahashi et al. | |
| 6,511,851 B1 | 1/2003 | Payne et al. | |
| 6,537,864 B1 * | 3/2003 | Aya | H01L 21/2022 438/166 |
| 6,537,927 B1 | 3/2003 | Son | |
| 6,825,734 B2 | 11/2004 | Clark | |
| 6,901,683 B2 | 6/2005 | Lyle et al. | |
| 7,133,180 B2 | 11/2006 | Ilchenko et al. | |
| 7,160,297 B2 | 1/2007 | Nesbitt | |
| 7,274,262 B2 | 9/2007 | Ham et al. | |
| 7,317,216 B2 | 1/2008 | Holm-Kennedy | |
| 7,393,501 B2 | 7/2008 | Zumeris et al. | |
| 7,429,719 B1 | 9/2008 | Spetz | |
| 7,586,381 B2 | 9/2009 | Rohde et al. | |
| 7,844,345 B2 | 11/2010 | Boling et al. | |
| 8,698,570 B2 | 4/2014 | Afshari et al. | |
| 8,933,416 B2 | 1/2015 | Arcand et al. | |
| 9,008,793 B1 | 4/2015 | Cosman, Sr. et al. | |
| 9,362,604 B2 | 6/2016 | Denis et al. | |
| 9,536,758 B1 | 1/2017 | Deo | |
| 10,431,478 B2 | 10/2019 | Deo | |
| 10,515,831 B2 | 12/2019 | Deo | |
| 10,553,462 B2 | 2/2020 | Deo | |
| 2002/0065052 A1 | 5/2002 | Pande et al. | |
| 2002/0120296 A1 | 8/2002 | Mech et al. | |
| 2003/0164371 A1 | 9/2003 | Bergstrom et al. | |
| 2003/0205571 A1 | 11/2003 | Flugstad et al. | |
| 2005/0068116 A1 | 3/2005 | Ham et al. | |
| 2005/0083785 A1 | 4/2005 | Shiokawa et al. | |
| 2006/0071237 A1 | 4/2006 | Deboy et al. | |
| 2007/0161263 A1 | 7/2007 | Meisner | |
| 2007/0260239 A1 | 11/2007 | Podhajsky et al. | |
| 2009/0054881 A1 | 2/2009 | Krespi | |
| 2009/0071952 A1 | 3/2009 | Kuwabara | |
| 2009/0131854 A1 | 5/2009 | DiCarlo et al. | |
| 2009/0162954 A1 | 6/2009 | Griffin, Jr. et al. | |
| 2009/0256649 A1 | 10/2009 | Taniguchi | |
| 2010/0030210 A1 | 2/2010 | Paulus | |
| 2010/0036375 A1 | 2/2010 | Regadas | |
| 2010/0036405 A1 | 2/2010 | Giordano et al. | |
| 2010/0191232 A1 | 7/2010 | Boveda | |
| 2010/0217259 A1 | 8/2010 | Strauss | |
| 2010/0249692 A1 | 9/2010 | Dacey, Jr. et al. | |
| 2010/0286691 A1 | 11/2010 | Kerr et al. | |
| 2011/0137390 A1 | 6/2011 | Hill | |
| 2011/0152790 A1 | 6/2011 | Dacey, Jr. et al. | |
| 2011/0226759 A1 | 9/2011 | Wander et al. | |
| 2012/0029500 A1 | 2/2012 | Jenson | |
| 2012/0152935 A1 | 6/2012 | Kitaizumi et al. | |
| 2012/0261405 A1 | 10/2012 | Kurose et al. | |
| 2012/0330393 A1 | 12/2012 | Janik et al. | |
| 2013/0096595 A1 | 4/2013 | Myhr et al. | |
| 2013/0282084 A1 | 10/2013 | Mathur et al. | |
| 2014/0088674 A1 | 3/2014 | Bradley | |
| 2014/0257272 A1 | 9/2014 | Clark, III et al. | |
| 2015/0119877 A1 | 4/2015 | Jameson et al. | |
| 2015/0289316 A1 * | 10/2015 | Shimizu | H05B 1/0233 438/795 |
| 2017/0258628 A1 | 9/2017 | Awasthi | |
| 2018/0042667 A1 | 2/2018 | Pappone et al. | |
| 2018/0323090 A1 | 11/2018 | Deo | |
| 2019/0109024 A1 | 4/2019 | Deo | |
| 2020/0013644 A1 | 1/2020 | Deo | |
| 2020/0118846 A1 | 4/2020 | Deo | |
| 2020/0135507 A1 | 4/2020 | Deo | |

FOREIGN PATENT DOCUMENTS

| | | |
|---|---|---|
| EP | 3113281 A1 | 1/2017 |
| GB | 1529941 A | 10/1978 |
| WO | WO-9600039 A1 | 1/1996 |
| WO | WO-2012153529 A1 | 11/2012 |
| WO | WO-2016181397 A1 | 11/2016 |
| WO | WO-2017204860 A1 | 11/2017 |
| WO | WO-2019010238 A1 | 1/2019 |
| WO | WO-2020010247 A1 | 1/2020 |

OTHER PUBLICATIONS

U.S. Appl. No. 16/200,120 U.S. Pat. No. 10,431,478, filed Nov. 26, 2018, Time-Varying Frequency Powered Heat Source.
U.S. Appl. No. 16/548,809, filed Aug. 22, 2019, Time-Varying Freuency Powered Heat Source.
U.S. Appl. No. 16/666,773, filed Oct. 29, 2019, Medical Instrument for In Vivo Heat Source.
U.S. Appl. No. 16/027,139 U.S. Pat. No. 10,515,831, filed Jul. 3, 2018, Medical Instrument for In Vivo Heat Source.
U.S. Appl. No. 16/502,989 U.S. Pat. No. 10,553,462, filed Jul. 3, 2019, Planar Transmission Line Resonator Frequency Control of Localized Transducers.
"U.S. Appl. No. 15/165,096, Notice of Allowance dated Aug. 31, 2016", 9 pgs.
"U.S. Appl. No. 16/027,139, Corrected Notice of Allowability dated Sep. 20, 2019", 3 pgs.
"U.S. Appl. No. 16/027,139, Examiner Interview Summary dated Jun. 21, 2019", 3 pgs.
"U.S. Appl. No. 16/027,139, Non Final Office Action dated Mar. 22, 2019", 13 pgs.
"U.S. Appl. No. 16/027,139, Non Final Office Action dated Nov. 19, 2018", 11 pgs.
"U.S. Appl. No. 16/027,139, Notice of Allowance dated Jul. 29, 2019", 8 pgs.
"U.S. Appl. No. 16/027,139, Response filed Dec. 10, 2018 to Non Final Office Action dated Nov. 19, 2018", 12 pgs.

(56) References Cited

OTHER PUBLICATIONS

"U.S. Appl. No. 16/027,139, Response filed Jun. 20, 2019 to Non-Final Office Action dated Mar. 22, 2019", 16 pgs.
"U.S. Appl. No. 16/200,120, Corrected Notice of Allowability dated Aug. 26, 2019", 2 pgs.
"U.S. Appl. No. 16/200,120, Examiner Interview Summary dated Apr. 11, 2019", 3 pgs.
"U.S. Appl. No. 16/200,120, Notice of Allowance dated May 22, 2019", 5 pgs.
"U.S. Appl. No. 16/200,120, Response filed Mar. 25, 2019 to Non-Final Office Action dated Jan. 24, 2019", 16 pgs.
"U.S. Appl. No. 16/200,120, Supplemental Response filed Apr. 8, 2019 to Non-Final Office Action dated Jan. 24, 2019", 10 pgs.
"U.S. Appl. No. 16/502,989, Corrected Notice of Allowability dated Oct. 31, 2019", 2 pgs.
"U.S. Appl. No. 16/502,989, Notice of Allowance dated Sep. 25, 2019", 9 pgs.
"U.S. Appl. No. 16/502,989, Preliminary Amendment filed Jul. 11, 2019", 4 pgs.
"European Application Serial No. 16903365.1, Extended European Search Report dated May 17, 2019", 8 pgs.
"International Application Serial No. PCT/US2016/069490, International Preliminary Report on Patentability dated Jul. 10, 2018", 1 pg.
"International Application Serial No. PCT/US2016/069490, International Search Report dated Mar. 8, 2017", 2 pgs.
"International Application Serial No. PCT/US2016/069490, Written Opinion dated Mar. 8, 2017", 7 pgs.
"International Application Serial No. PCT/US2018/040812, International Search Report dated Sep. 19, 2018", 2 pgs.
"International Application Serial No. PCT/US2018/040812, Written Opinion dated Sep. 19, 2018", 6 pgs.
"International Application Serial No. PCT/US2019/040588, International Search Report dated Oct. 8, 2019", 2 pgs.
"International Application Serial No. PCT/US2019/1040588, Written Opinion dated Oct. 8, 2019", 5 pgs.
Beringer, Robert, "The Measurement of Wavelength—Chapter 5 from Technique of Microwave Measurements", vol. 11 of MIT Radiation Laboratory Series. McGraw-Hill, New York, (1947), 58 pgs.
Gopinath, A., et al., "Capacitance Parameters of Discontinuities in Microstriplines", IEEE Trans. on Microwave Theory and Techniques, vol. MTT-26, No. 10, (Oct. 1978), 831-836.
Mahan, Gerald, et al., "Thermoelectric Materials: New Approaches to an Old Problem", Physics Today, (Mar. 1997), 42-47.
Otoole, Ann, et al., "Thermal mitigation of Pseudomonas aeruginosa biofilms", Biofouling. Sep. 2015; 31(8): 665-675., (2015), 20 pgs.
Richardson, Ian P., et al., "Hemodialysis Catheter Heat Transfer for Biofilm Prevention and Treatment", ASAIO J. 2016; 62(1): 92-99, doi:10.1097/Mat.0000000000000300, (2016), 17 pgs.
"U.S. Appl. No. 16/027,139, Corrected Notice of Allowability dated Oct. 29, 2019", 3 pgs.
"U.S. Appl. No. 16/548,809, Preliminary Amendment filed Jan. 6, 2020", 6 pgs.
"U.S. Appl. No. 16/666,773, Preliminary Amendment filed Jan. 21, 2020", 7 pgs.
"International Application Serial No. PCT/US2018/040812, International Preliminary Report on Patentability dated Jan. 16, 2020", 8 pgs.
"European Application Serial No. 18827857.6, Extended European Search Report dated Jul. 13, 2020", 6 pgs.
"European Application Serial No. 19830071.7, Extended European Search Report dated Aug. 16, 2021", 8 pgs.

* cited by examiner

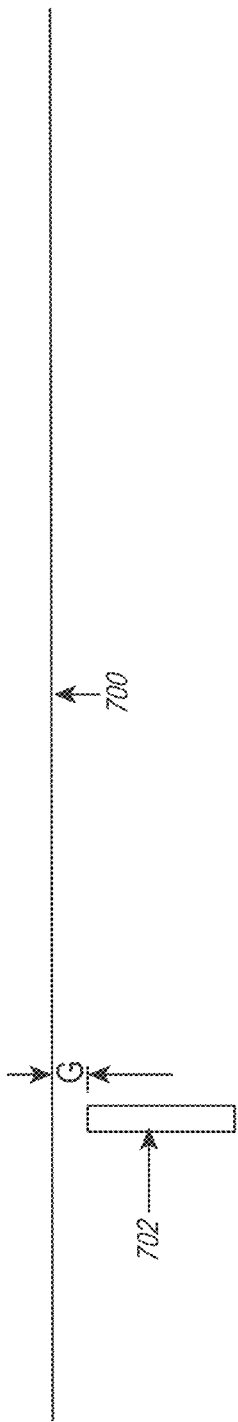
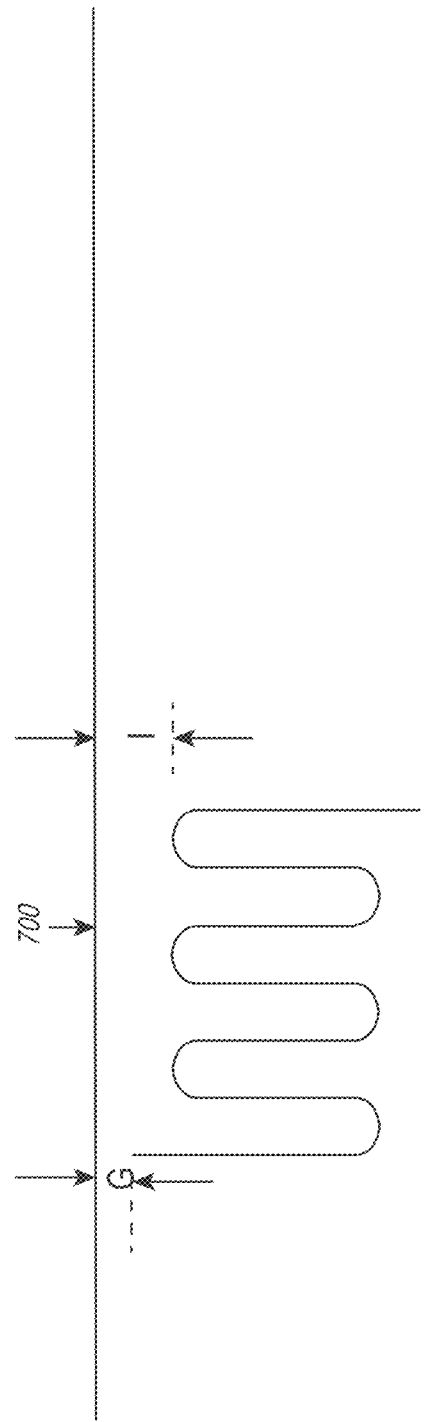

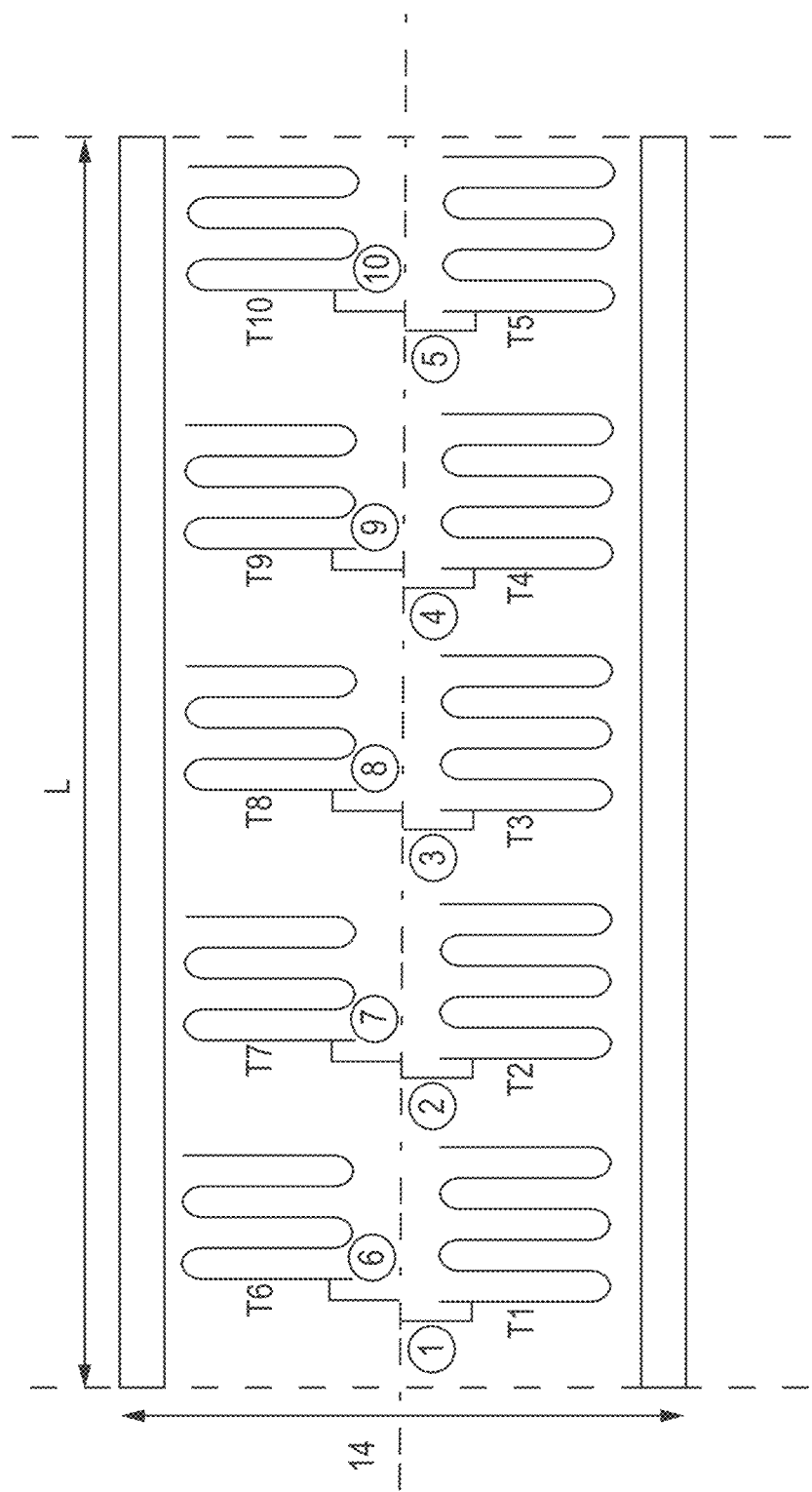

| 2.0 Ghz ⑥<br>T6 | 2.2 Ghz ⑦<br>T7 | 2.4 Ghz ⑧<br>T8 | 2 Ghz ⑨<br>T9 | 2.8 Ghz ⑩<br>T10 |
|---|---|---|---|---|
| 1 Ghz ①<br>T1 | 1.19 Ghz ②<br>T2 | 1.2 Ghz ③<br>T3 | 1.3 Ghz ④<br>T4 | 1.6 Ghz ⑤<br>T5 |

*FIG. 14C*

FREQUENCY AND PHASE CONTROLLED TRANSDUCERS AND SENSING

CLAIM OF PRIORITY

This application is a continuation-in-part of U.S. patent application Ser. No. 16/502,989 filed on Jul. 3, 2019, which is a continuation U.S. patent application Ser. No. 16/027,139 (now issued as U.S. Pat. No. 10,515,831) filed on Jul. 3, 2018 and also claims priority to U.S. Provisional Patent Application No. 62/693,881 filed on Jul. 3, 2018; is also a continuation-in-part of U.S. patent application Ser. No. 16/666,773 filed on Oct. 29, 2019, which is a continuation of Ser. No. 16/027,139 (now issued as U.S. Pat. No. 10,515,831) filed on Jul. 3, 2018, claims the benefit of 62/530,035 filed on Jul. 7, 2017, is a continuation-in-part of PCT/US2016/069490 filed on Dec. 30, 2016 and is a continuation of Ser. No. 15/165,096 filed on May 26, 2016 (now issued as U.S. Pat. No. 9,536,758), all of which are hereby incorporated by reference in their entireties, and the benefit of priority of each which is hereby claimed.

TECHNICAL FIELD

This document pertains to selecting or adjusting frequency of an AC electromagnetic input signal to select a path of signal flow transmitted along a main-line and further to selectively address and energize a transducer at a desired location along the selected path.

BACKGROUND

The wavelength of a RF/Microwave signal can be measured using a reaction cavity, which can be tunable and connected to a shunt, such as explained in "Technique of Microwave Measurements, volume 11 of MIT Radiation Laboratory Series. McGraw-Hill, New York, 1947, Chapter 5".

US 20070161263 RESONANT FREQUENCY FILTERED ARRAYS FOR DISCRETE ADDRESSING OF A MATRIX uses a substrate and intersecting frequency filtered arrays. A material is located between such arrays and changes a property in response the stimulus received simultaneously from both arrays. A resonance is between the two arrays.

U.S. Pat. No. 7,133,180 RESONANT IMPEDANCE MATCHING IN MICROWAVE AND RF DEVICE discusses devices and techniques for using microwave or RF resonators to provide DC bias, DC blocking, and impedance matching to microwave or RF devices.

U.S. Pat. No. 9,362,604 RF PLANAR FILTER HAVING RESONATOR SEGMENTS CONNECTED BY ADJUSTABLE ELECTRICAL LINKS defines an adjustable radio frequency filter in planar technology.

EP 3 113 281 COUPLING ELEMENT AND CAVITY RESONATOR DEVICE WITH A COUPLING ELEMENT relates to coupling two adjacent cavity resonators.

WO2012153529 ELECTROMAGNETIC RESONANCE COUPLER provides an electromagnetic resonance coupler that contactlessly transmits a high-frequency signal between two resonance wirings.

U.S. Pat. No. 7,274,262 METHODS AND APPARATUS BASED ON COPLANAR STRIP LINES relates to a standing wave oscillator to generate at least one voltage standing wave, comprising a closed-loop coplanar strip line including two conductors, and at least one amplifier disposed between the two conductors at a first location.

GB 1529941 mentions using a transducer to drive coupled resonators to form a surface wave filter.

U.S. Pat. No. 9,536,758 TIME VARYING FREQUENCY POWERED SEMICONDUCTOR SUBSTRATE HEAT SOURCE, US 2019-0109024 TIME VARYING FREQUENCY POWERED HEAT SOURCE, each of which is incorporated herein by reference in its entirety, relate to selecting a frequency of an applied input signal to select a location along a length of variable spacing between two or more individual electrodes to generate heat and control temperature gradient in an adjacent substrate.

SUMMARY

Particularly in applications in which available space on a device is constricted (such as in an implantable or insertable catheter or similar device) localized transducer addressing and energizing may be desired, such as in an application that can include one or a plurality of localized transducers. For example, the localized transducer can include at least one of a electromagnetic-to-heat transducer or an electromagnetic-to-vibration transducer. In certain applications, the underlying process may be best served by breaking the process into distinct steps in time or space, or both. In certain applications, there is a need to selectively control energy flow path or deposition of energy, or both, such as at one or more distinct steps in time or space. Some approaches for selectively addressing and energizing a local transducer can according to a desired pattern in time, in space, or in both time and space, can require independent access to the transducer, such as via multiple electrically conductive main-lines that are connected to a power source. But the need to have many independent power paths can be bulky and impractical.

The present inventor has recognized, among other things, that it is possible to select or adjust the frequency of an applied AC electromagnetic input signal to select an energy flow path and to control the amount of energy that is delivered via the selected energy flow path, which is possible using a single main-line as input, if desired. Such an approach can reduce the number of input power main lines and can also help enable extremely fast operating or reaction times. The input signal can self-select its path governed by its frequency and the characteristic frequency of the destination structure, without the need for any oscillator, secondary control mechanism, signaling or communication between the source and destination of the input signal.

For example, a transmission line based control device for an integrated transducer can be constructed. The device can include a substrate. The substrate can provide a transducer, which can be integrated and coupled with a transmission line resonator. The resonator can be configured to receive an AC electromagnetic input signal directly, or via an electrically conductive main-line coupled with the resonator. The resonator can be configured to resonate at its characteristic AC electromagnetic input signal frequency, such as to energize the coupled substrate transducer at a first energy level. The resonator can also be configured to be off-resonance at a frequency that is different from its characteristic AC electromagnetic input signal frequency, such as to energize the coupled substrate transducer at a second energy level that is less than the first energy level. This arrangement and technique can provide variable frequency control of energizing the transducer. The electromagnetic wave resonates in the transmission line resonator at its characteristic frequency because the wavelength, half-wavelength, or quarter-wavelength is equal to or close to the length of the transmission line resonator.

Similarly, the device can be constructed to include a plurality of resonators. These resonators can be respectively co-located with corresponding transducers, at different locations along the main-line. An individual first one of the resonators can be configured to resonate at a first characteristic AC electromagnetic input signal frequency to energize the co-located first one of the transducers. An individual second one of the resonators can be configured to be off-resonance at the first characteristic AC electromagnetic input signal frequency, to energize the co-located second one of the electromagnetic-to-heat transducers less than the first transducer at the first characteristic AC electromagnetic input signal frequency. The transducers may include electromagnetic-to-heat transducers, such that the second transducer generates less heat than the first transducer at the first characteristic AC electromagnetic input signal frequency. The substrate may include a lossy dielectric substrate, in an illustrative example.

In an example of the present approach, a RF or other AC electromagnetic input signal can be transmitted through an electrical conductor or a main-line as a source of power. Such main-lines can cover a spatial geometry (for example along at the length of an instrument such as a tube or catheter). In certain applications, it is desired to trigger or transfer power at different points or locations along a single main-line for use by a transducer or other load, such as for example in an application including but not limited to heating using an electromagnetic-to-heat transducer. The present document describes using a planar resonator transmission line to create or control such a spatiotemporal distribution of power using the frequency of the RF signal for control.

In an example of the present approach, a fixed frequency resonator can act as a frequency dependent RF cavity. An AC electromagnetic input signal can be applied to the main-line and produces an amplitude dip at the fixed characteristic frequency of the resonator, thereby creating an energy flow path that is frequency specific. When a plurality of resonators of various characteristic resonance frequencies are arranged along the main-line, only the resonator(s) having a characteristic resonance frequency that matches the frequency of the applied AC electromagnetic input signal will react by resonating, while the other off-resonance resonators arranged along the main-line will reflect the applied AC electromagnetic input signal at such an applied frequency. In this way, many different frequency dependent paths can be established for the AC electromagnetic input signal and energy along a particular shared main-line. Each path can correspond to one or more resonators that are addressable by varying the frequency of the applied AC electromagnetic input signal to match a specific corresponding resonance frequency of one or more desired resonators to be addressed. The resonators can be coupled to a corresponding local transducer (such as can be provided by an adjacent substrate), such as an electromagnetic-to-heat transducer, or an electromagnetic-to-vibration transducer, or both, such as to energize the desired local transducer to a desired energization level by selecting or adjusting the frequency of the applied AC electromagnetic input signal. In this way, a desired amount of heat or vibration can be generated at one or more desired locations, such as by selecting or adjusting the frequency of the applied AC electromagnetic input signal.

Although some description of this document is focused toward a resonator that can be coupled to an output transducer (e.g., an electromagnetic-to-heat transducer, or electromagnetic-to-vibration transducer), the present subject matter can additionally or alternatively include or use an input transducer (such as a sensor). For example, an external environment can be sensed by measuring a differential reflection of the applied AC electromagnetic input signal, or by measuring a transfer of energy of the applied AC electromagnetic input signal between the transducer coupled to the resonator and a surrounding environment. For example, in an in vivo catheter application, blood and tissue have different dielectric constants. Blood has a dielectric constant (or relative permittivity) of about 80 and tissue has a dielectric constant of about 40. Therefore, between a substrate transducer in a polyurethane catheter having a dielectric constant of about 2.2 and the surrounding blood or tissue, differential energy reflection can be sensed, such as to characterize the environment surrounding the tissue. Also, other forms of output transducers can be controlled by a resonator integrated to excite or energize the transducer, for example, a piezoelectric pressure transducer, a pn junction diode or light-emitting-diode or other circuitry included within a semiconductor substrate can be energized and controlled by applying an AC electromagnetic input signal to a resonator that can be coupled to such a transducer or other circuitry.

Although some description of this document is focused toward a specific application of this planar resonator approach to generating localized heat for sterilizing a catheter, it should be understood that the present approach will permit many other applications as well, with the catheter or tube heating serving as an illustrative non-limiting specific example. A further illustrative, non-limiting numbered list of various aspects of the present subject matter is provided below.

Aspect 1 can include or use subject matter (e.g., device, apparatus, method, machine-readable medium for implementing a method, or the like) that can provide a transmission line based control device for an integrated transducer. In an example, this can include or use a substrate (e.g., semiconductor, lossy dielectric, piezoelectric, or the like) providing the transducer, coupled to a resonator. The resonator (e.g., a planar resonator) can be configured to receive an AC electromagnetic (e.g., electrical) input signal, such as directly, or via an electrically conductive main line that can be coupled (e.g., electrically connected, inductively coupled, capacitively coupled or hybrid (e.g., inductively and capacitively) coupled) with the resonator. The resonator can be configured to resonate at its characteristic AC electromagnetic input signal frequency, such as to energize the transducer at a first energy level. The resonator can also be configured to be off-resonance at an AC electromagnetic input signal frequency different from its characteristic (resonance) AC electromagnetic input signal frequency, such as to energize the transducer at a second energy level that is less than the first energy level. In this way, variable frequency control of energizing the transducer can be provided, such as by selecting or varying the frequency of the AC electromagnetic input signal.

Aspect 2 can include or use, or can optionally be combined with the subject matter of Aspect 1, such as can include or use a transducer that can include at least one of an electromagnetic-to-heat transducer (e.g., via a semiconductor or other lossy dielectric substrate coupled to the resonator) or an electromagnetic-to-vibration transducer (e.g., via a piezoelectric substrate coupled to the resonator).

Aspect 3 can include or use, or can optionally be combined with the subject matter of any of Aspects 1 or 2, such as can include or use a plurality of resonators. Individual resonators can respectively be co-located with corresponding transducers (e.g., such as corresponding electromagnetic-to-heat transducers) at different locations along the main line. The substrate can include a piezoelectric or a lossy dielectric substrate (or substrate portion), such as adjacent to the resonator, thereby providing the transducer under control of the resonator. An individual first one of the resonators can be configured to resonate at a first characteristic AC electromagnetic input signal frequency, such as to energize (e.g., to generate heat in the substrate) the co-located first one of the electromagnetic-to-heat transducers. An individual second one of the resonators can be configured to be off-resonance at the first characteristic AC electromagnetic input signal frequency, to energize less, e.g., generate less heat in the substrate at the co-located second one of the electromagnetic-to-heat transducers than is generated in the first one of the electromagnetic-to-heat transducers at the first characteristic AC electromagnetic input signal frequency.

Aspect 4 can include or use, or can optionally be combined with the subject matter of any of Aspects 1 through 3, such as can include or use a tap-line between the resonator and the main line. The tap-line can be arranged to provide an electrically conductive or inductively-coupled connection between the resonator and the main line.

Aspect 5 can include or use, or can optionally be combined with the subject matter of any of Aspects 1 through 4, such as can include or use a capacitive coupler between the resonator and the main line. The capacitive coupler can be arranged to provide a capacitively-coupled connection between the resonator and the main line. For example, the capacitive coupler can include an air gap or a dielectric gap between the electrically conductive portions of the resonator and the main line, which can be co-planar (e.g., within the same layer with a gap therebetween) or in different planes (e.g., in different layers, with a gap therebetween).

Aspect 6 can include or use, or can optionally be combined with the subject matter of any of Aspects 1 through 5, such as can include or use a hybrid coupler between the resonator and the main line. The hybrid coupler can be arranged to provide, e.g., in series, both of: (1) an electrically conductive or inductively-coupled connection between the resonator and the main line; and (2) a capacitively-coupled connection between the resonator and the main line.

Aspect 7 can include or use, or can optionally be combined with the subject matter of any of Aspects 1 through 6, such as can include or use a second resonator, arranged in series with or in a cascade with the first resonator such as to share at least one of a tap-line, a capacitive coupler, or a hybrid coupler with the first resonator.

Aspect 8 can include or use, or can optionally be combined with the subject matter of any of Aspects 1 through 7, such as can include or use first and second resonators that are configured to be independently addressed using different characteristic AC electromagnetic input signal frequencies.

Aspect 9 can include or use, or can optionally be combined with the subject matter of any of Aspects 1 through 8, such as can include or use a plurality of resonators. Respective ones of the resonators can be arranged to provide sufficient frequency-domain spacing between corresponding characteristic AC electromagnetic input signal frequencies of corresponding resonators such that desired ones or groups of the resonators are selectively addressable by applying a variable frequency of the received AC electromagnetic input signal (e.g., without addressing other (e.g., non-desired) ones or groups of the resonators at that applied frequency of the received AC electromagnetic input signal.

Aspect 10 can include or use, or can optionally be combined with the subject matter of any of Aspects 1 through 9, such as can include or use the resonator such as can be configured such that its characteristic AC electromagnetic input signal frequency is configured including based on a property of the substrate in composite with a property of an operating environment in which the resonator is to be located. For example, a resonance frequency or dissipated power of the resonator may depend upon a composite permittivity of the substrate in combination with a permittivity of the operating environment in which the resonator and substrate are placed, e.g., a permittivity of a catheter or other carrying device, a permittivity of surrounding tissue or blood or both or other environment in which the carrying device is placed, or the like.

Aspect 11 can include or use, or can optionally be combined with the subject matter of any of Aspects 1 through 10, such as can include or use the resonator such as can include a planar resonator arranged in a flat or curved plane within a lossy dielectric or other active substrate or with the lossy dielectric or other active substrate facing each opposing surface of the flat or curved plane. For example, the planar resonator can include a planar resonator line arranged in a strip-line configuration, or embedded in a substrate that can include one or more lossy dielectric portions, such as can serve as electromagnetic-to-heat transducers controlled by the planar resonator line such as by providing a selected or adjustable frequency of a received AC electromagnetic input signal.

Aspect 12 can include or use, or can optionally be combined with the subject matter of any of Aspects 1 through 11, such as can include or use the resonator such as can include a planar resonator arranged in a flat or curved plane. A thickness of the (e.g., lossy dielectric) substrate, with respect to at least one electrically conductive portion of the planar resonator or with respect to an operating environment, can vary with respect to at least one of different locations of electrically conductive portions of the planar resonator within the resonator. For example, such variable thickness of the substrate can make portions of an electromagnetic-to-heat transducer provided by the substrate to be hotter (or colder) than other portions of the electromagnetic-to-heat transducer provided by the substrate.

Aspect 13 can include or use, or can optionally be combined with the subject matter of any of Aspects 1 through 12, such as can include or use the substrate that can include a more lossy first dielectric portion adjacent to the planar resonator than a less lossy second dielectric portion that is adjacent to the main line.

Aspect 14 can include or use, or can optionally be combined with the subject matter of any of Aspects 1 through 13, such as can include or use a method of using a transmission line based control device to control a transducer. The method can include receiving an AC electromagnetic input signal. The received AC electromagnetic input signal can be used at a first frequency such as to resonate a resonator at a characteristic AC electromagnetic input signal frequency to energize the transducer at a first energy level. The received AC electromagnetic input signal can be used at a second frequency such as to put the resonator off-resonance at a frequency different from the characteristic AC electromagnetic input signal frequency such as to energize the transducer at a second energy level that is less than the first energy level. In this way, variable frequency control of energizing the transducer can be provided, such as by selecting or adjusting the frequency of the AC electromagnetic input signal.

Aspect 15 can include or use, or can optionally be combined with the subject matter of any of Aspects 1 through 14, such as can include or use energizing the transducer such as by including at least one of heating or vibrating.

Aspect 16 can include or use, or can optionally be combined with the subject matter of any of Aspects 1 through 15, such as can include or use receiving the AC electromagnetic input signal at a first resonator, such as at its first characteristic AC electromagnetic input signal frequency, to energize a first transducer co-located with the first resonator (e.g., such as in a substrate adjacent to the first resonator). The AC electromagnetic input signal can be received to be off-resonance at a second resonator, at the first characteristic AC electromagnetic input signal frequency, such as to energize a second transducer co-located with the second resonator (e.g., such as in a substrate adjacent to the second resonator) at a level less than that of the first transducer.

Aspect 17 can include or use, or can optionally be combined with the subject matter of any of Aspects 1 through 16, such as can include or use at least one of inductively coupling the received AC electromagnetic input signal to the resonator or capacitively coupling the received AC electromagnetic input signal to the resonator.

Aspect 18 can include or use, or can optionally be combined with the subject matter of any of Aspects 1 through 17, such as can include or use independently addressing first and second resonators having different characteristic AC electromagnetic input signal frequencies by receiving a variable frequency of the received AC electromagnetic input signal.

Aspect 19 can include or use, or can optionally be combined with the subject matter of any of Aspects 1 through 18, such as can include or use an apparatus or method for sensing a material characteristic of a target region. This can include applying a time-varying electromagnetic signal to first and second electrical conductor terminals defining a first layer for electrical conduction in the first layer. The electrical conductor can be embedded in the active substrate, e.g., as a layer, thus the two layers may not be easily discernable. The signal entry components form the first layer. This can also include generating heat in an active substrate second layer, adjacent to the first layer, in response to the applying the time-varying electromagnetic signal. This can also include transferring heat from the active substrate second layer to the target region, the target region including a portion that is adjacent to the active substrate second layer. This can also include measuring a temperature at a one or more measurement locations corresponding to the electrical conduction in the first layer. This can also include computing an indication of the material characteristic of the target region corresponding to the one or more measurement locations based on the measured temperature.

Aspect 20 can include or use, or can optionally be combined with the subject matter of any of Aspects 1 through 19, such as can include or use measuring first and second temperatures at different first and second measurement locations corresponding to the electrical conduction in the first layer. An indication of the material characteristic of the target region can include computing the indication based upon the measured first and second temperatures.

Aspect 21 can include or use, or can optionally be combined with the subject matter of any of Aspects 1 through 20, such as can include or use computing the indication of the material characteristic of the target region based upon a difference between the measured first and second temperatures.

Aspect 22 can include or use, or can optionally be combined with the subject matter of any of Aspects 1 through 21, such as can include or use computing the indication of the material characteristic of the target region such as to include computing an indication of a dielectric permittivity.

Aspect 23 can include or use, or can optionally be combined with the subject matter of any of Aspects 1 through 22, such as can include or use computing the indication of the material characteristic of the target region including classifying the indication to a material type at the measurement location of the target region.

Aspect 24 can include or use, or can optionally be combined with the subject matter of any of Aspects 1 through 23, such as can include or use classifying the indication to a material type including classifying the material as into one of a plurality of material types at the location of the target region, the plurality of material types including at least two of blood, bone, calcium, tissue, and tissue type (e.g., bone, muscle, fat, or the like).

Aspect 25 can include or use, or can optionally be combined with the subject matter of any of Aspects 1 through 24, such as can include or use a plurality of material types including different types of tissue.

Aspect 26 can include or use, or can optionally be combined with the subject matter of any of Aspects 1 through 25, such as can include or use adjusting a frequency of the applied time-varying electromagnetic signal to adjust a heating location in the active substrate second layer.

Aspect 27 can include or use, or can optionally be combined with the subject matter of any of Aspects 1 through 26, such as can include or use measuring the temperature at a measurement location corresponding to the electrical conduction in the first layer comprising measuring temperature at a measurement location corresponding to the adjusted heating location.

Aspect 28 can include or use, or can optionally be combined with the subject matter of any of Aspects 1 through 27, such as can include or use an electromagnetic heating sensor apparatus to sense a material characteristic of a target region. The apparatus can include or use first and second electrical conductor terminals defining a first layer for electrical conduction in the first layer in response to an applied electromagnetic signal. An active substrate second layer can be located adjacent to the first layer, the active substrate second layer can be configured to generate heat, in response to the applying the electrical signal, at a heating location specified according to a frequency of the applied electromagnetic signal. One or more temperature sensors can be configured to measure temperature at one or more corresponding measurement locations corresponding to the one or more corresponding heating locations for communication to a signal processor circuit that is configured process a signal representing the measured temperature and compute an indication of the material characteristic of the target region based on the measured temperature.

Aspect 29 can include or use, or can optionally be combined with the subject matter of any of Aspects 1 through 28, such as can include or use the signal processor circuit. The signal processor circuit can be configured to compute an indication of the material characteristic of the target region based on measured first and second temperatures taken at different first and second measurement locations corresponding to the electrical conduction in the first layer.

Aspect 30 can include or use, or can optionally be combined with the subject matter of any of Aspects 1 through 29, such as can include or use the signal processor circuit being configured to compute the indication of the material characteristic of the target region based upon a difference between the measured first and second temperatures.

Aspect 31 can include or use, or can optionally be combined with the subject matter of any of Aspects 1 through 30, such as can include or use the signal processor circuit. The signal processor circuit can be configured to compute the indication of the material characteristic of the target region including computing an indication of a dielectric permittivity.

Aspect 32 can include or use, or can optionally be combined with the subject matter of any of Aspects 1 through 31, such as can include or use the signal processor circuit. The signal processor circuit can be configured to classify the indication to a material type at the measurement location of the target region.

Aspect 33 can include or use, or can optionally be combined with the subject matter of any of Aspects 1 through 32, such as can include or use the signal processor circuit being configured to classify the indication into one of a plurality of material types at the location of the target region, for example, the plurality of material types including blood and tissue.

Aspect 34 can include or use, or can optionally be combined with the subject matter of any of Aspects 1 through 33, such as can include or use the plurality of material types including different types of tissue.

Aspect 35 can include or use, or can optionally be combined with the subject matter of any of Aspects 1 through 34, such as can include or use controller circuitry such as can be configured for adjusting a frequency of the applied time-varying electromagnetic signal to adjust a heating location in the active substrate second layer.

Aspect 36 can include or use, or can optionally be combined with the subject matter of any of Aspects 1 through 35, such as can include or use the signal processing circuit being configured for measuring the temperature at a measurement location corresponding to the electrical conduction in the first layer, wherein the measurement location corresponds to the adjusted heating location.

Aspect 37 can include or use, or can optionally be combined with the subject matter of any of Aspects 1 through 36, such as can include or use a heating apparatus or method to heat a target region. This can include or use applying a time-varying electromagnetic signal to first and second electrical conductor terminals defining a first layer for electrical conduction in the first layer. This can also include or use generating heat in an active substrate second layer, adjacent to the first layer, in response to the applying the time-varying electromagnetic signal. This can also include or use heating the target region, the target region including a portion that is adjacent to the active substrate second layer, wherein the heating creates a temperature profile that is hotter in the active substrate second layer than in the first layer for heating the target region by transferring heat to the target region from the active substrate second layer.

Aspect 38 can include or use, or can optionally be combined with the subject matter of any of Aspects 1 through 37, such as can include or use an electromagnetic heating apparatus to heat a target region. This can include or use first and second electrical conductor terminals defining a first layer for electrical conduction in the first layer in response to an applied electromagnetic signal. This can also include or use an active substrate second layer, adjacent to the first layer, the active substrate second layer configured to generate heat, in response to the applying the electrical signal at a heating location specified according to a frequency of the applied electromagnetic signal, the heat generated with a temperature profile that is hotter in the active substrate second layer than in the first layer for heating the target region by transferring heat to the target region from the active substrate second layer.

These illustrative aspects and the present Summary are intended to give a brief overview, with further explanation provided below.

BRIEF DESCRIPTION OF THE DRAWINGS

FIGS. 13B-13E show illustrative examples of capacitive loading.

FIG. 14C shows a simplified top view of the unrolled cylindrically planar surface of the catheter showing a grid indicating the general arrangement of the ten planar resonators (T1, . . . , T10) together with their corresponding characteristic resonance frequencies that can be used to selectively address and actuate the planar resonators T1, . . . , T10, either individually, or in groups.

DETAILED DESCRIPTION

Figure 1A:
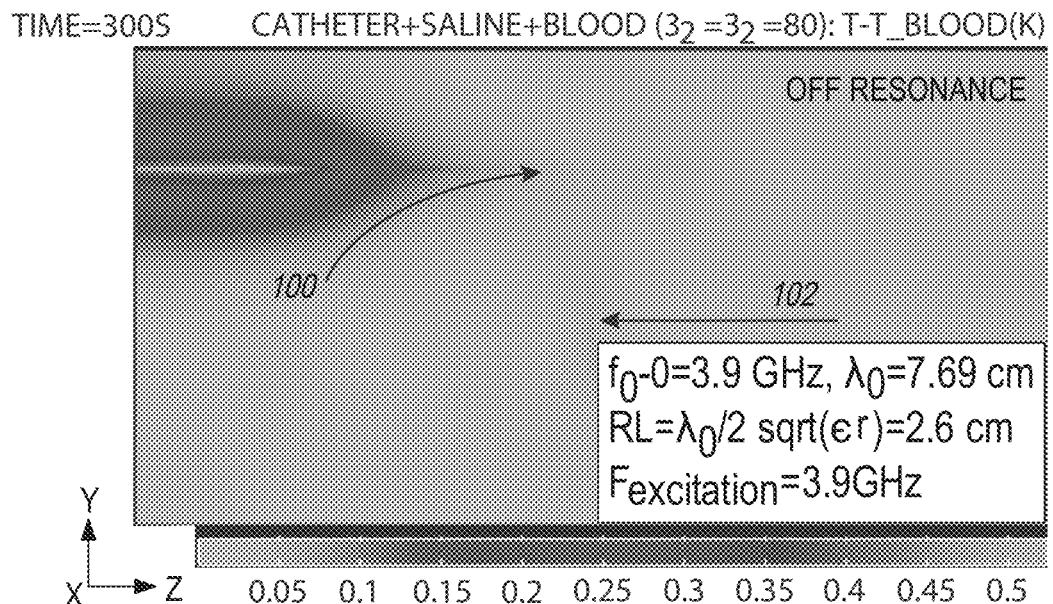
FIGS. 1A-1B shows computer-simulation results of on and off resonance temperature field after power is supplied to a computer-modeled main line coupled to a computer-modeled planar resonator coupled to a computer-modeled transducer in an adjacent substrate.

This document describes, among other things, how localized heating can use a fixed-frequency planar transmission line resonators arranged along a main-line, selected by tuning an electromagnetic input signal frequency applied to the main line for depositing heat in an adjacent active substrate. More generally, adjusting input signal frequency can be used to selectively address and energize an electromagnetic-to-heat, an electromagnetic-to-vibration, or other transducer to controllably direct energy toward a desired transducer load. Resonators or other electromagnetically energized transducers can be arranged to electromagnetically interfere, such that specifying or adjusting a relative phase of applied electrical signals can be used to specify or adjust the energy directed toward a desired transducer load. Temperature sensing can characterize a material in a target region near the transducer. A cold-hot-cold temperature profile can better manage temperature and avoid overheating a dielectric material such as the active substrate material.

Planar Resonator Approach

In the context of the present planar resonator techniques, the following terminology may be helpful. A "main line" can be used to refer to an electrically conductive signal line that can transmit an RF or other AC electromagnetic input signal from its source into an object. A "planar resonator line" can be used to refer to an electrically conductive signal line, such as of specified length, that resonates in response to a predefined or specified signal frequency. The "planar resonator line" need not be confined to a planar or cylindrically co-planar arrangement. A "tap line" can be used to refer to an electrically conductive signal line that electrically connects or inductively couples the main line and the planar resonator line. In an example, the tap line can optionally include a frequency selective filter element, such as a frequency selective crystal selected to pass a signal at the characteristic resonance frequency of the corresponding planar resonator, such as can help avoid excessive loading of the main line when multiple planar resonators are connected thereto, however, this is not required. The planar resonator line can alternatively be capacitively coupled to the main line via a capacitive coupler. For example, the capacitive coupler can include a capacitance created by a dielectric gap or air gap between two electrical conductors, with the gap between such conductors being located within the same plane or layer, or between such conductors being located in different planes or layers. The planar resonator line can be coupled to the main line using a hybrid coupler, which can combine the tap-line and capacitive coupler approaches. A "ground line" can be used to refer to an electrically conductive signal line that acts as an electrical ground. A "planar resonator" can be sometimes referred to herein more succinctly as a "resonator," and can be used to refer to a combination that can include a tap line (or capacitive or hybrid coupler), a planar resonator line, and optionally a ground line.

The main line, the planar resonator line, the tap line (or capacitive or hybrid coupler), the ground line and other connecting lines, if any, can all be placed either in a coplanar (including cylindrically coplanar) or strip-line configuration, such as on or within an active semiconductor or other substrate of the ultimate application object (e.g., an electromagnetic-to-heat transducer heating device) or the load. The planar resonator can act as a shunt cavity. The length of the planar resonator line can be fabricated to resonate at a characteristic resonance frequency, which can be specified to correspond to a specified multiple of a quarter of the wavelength ($\lambda/4$) of an addressing frequency of an AC electromagnetic input signal (when the planar resonator is grounded) or to correspond to a specified multiple of a half of the wavelength ($\lambda/2$) of an addressing frequency of an AC electromagnetic input signal (when the planar resonator is non-grounded, e.g., is in an open-ended non-grounded circuit configuration). The tap line (or capacitive or hybrid coupler), its impedance, and the position of its electrical connection or coupling between the main line and the planar resonator can be configured so as to help increase or maximize the power flow into the planar resonator at resonance at its designated characteristic resonance frequency and to help reduce or minimize the power flow into the planar resonator off-resonance at frequencies other than at its designated characteristic resonance frequency (e.g., for example at a different resonance frequency of one or more other planar resonators that are also electrically connected (or capacitively coupled) to the main line. By appropriately selecting tap-line (or capacitive or hybrid coupler) impedance in this way, a particular planar resonator need not place a significant load on the main line when the electrical signal on the main line is of a frequency different from the characteristic resonance frequency of that planar resonator. This can help promote or ensure power flow past a non-addressed planar resonator to help the power reach and flow into another planar resonator, also coupled to the main line, when such other planar resonator is at resonance.

At resonance, energy flows and is trapped in a resonator cavity. The present inventor has recognized, among other things, the effect of reflection off-resonance to keep power from entering the resonator. More particularly, off-resonance, the reflected waves can be useful because they can have the effect of inhibiting or preventing power from entering the resonator, as confirmed by the computer-modeled simulation results and described with respect to FIG. 1 of the present document.

Thus, it is possible to control flow of power into a conductor or transmission line by adjusting frequency rather than by adjusting current and voltage. Adjusting frequency effectively adjusts the wavelength of the electromagnetic wave. A transmission line has a characteristic resonance frequency, which may depend in part on the specific environment in which the transmission line is placed (e.g., placed in a polyurethane wall, in blood and tissue, as compared to being placed in air or in a vacuum. At resonance, the transmission line behaves as a cavity because stationary waves trap power in the transmission line.

A single transmission line, such as a Goubau line, can be connected to a signal source, with or without termination. At resonance, power will concentrate in the transmission line by creating stationary waves. Off-resonance, power will be reflected back toward the source. The location of power concentration is limited to the path of the transmission line. Thus, by altering frequency of the AC electromagnetic input signal one can adjust the amount of power sustained in the single transmission line resonator. In applications such as in which a return path for current is an impediment, such an approach can offer a versatile option. For example, in case of a catheter, such as where the tip of the catheter is, in practice, cut to suit the patient's anatomical features, a traditional electrical circuit requiring a return path would not work, because it would be disabled due to the open circuit that would be created when the tip of the catheter is cut off.

The present inventor has further recognized that this single transmission line approach can be extended, such as by electromagnetically coupling multiple resonator segments to a main-line. Each such resonator has its own characteristic resonance frequency. By altering the frequency of the applied AC electromagnetic input signal, one can move power concentration from one resonator to another resonator along the main-line. The resonator having a characteristic frequency that matches the AC electromagnetic input signal frequency of the source will effectively pull power into itself, while off-resonance counterparts will inhibit or prevent power from entering. In this configuration, the selected frequency of the AC electromagnetic input signal can control both location or path of power flow or signal flow and the quantity of power at various resonator locations along the main-line as opposed to at the entire main-line.

Various planar resonator structures can be included along a catheter, with the one or more planar resonators being addressed by a particular frequency of an applied AC electromagnetic input signal creating a transmission line cavity at that particular frequency, with one or more non-addressed planar resonators reflecting the excitation of the applied AC electromagnetic input signal at that particular frequency. It can be referred to as "planar" because it is a relatively flat transmission line cavity, rather than a spatial transmission line cavity such as would be used in a microwave oven. The flat plane can be curved, for example, wrapped around a circumference of a catheter or other cylindrical or tubular structure, such as explained elsewhere herein.

In a planar resonator approach, an RF or like AC electromagnetic input signal can be transmitted through an electrical conductor, which can be referred to as "a main line" as a source of power for one or more frequency-addressable planar resonators that can be capacitively or inductively or hybrid coupled to the main-line. The individual planar resonators can be coupled (e.g., via a substrate) to a corresponding adjacent or nearby transducer, such as an electromagnetic-to-heat transducer in a lossy dielectric substrate, such as to provide localized heat generation, such as within or on a catheter or other object upon which the planar resonators are located. Individual planar resonators can be selectively patterned, such as including a selectively patterned electrical conductor within an electrode layer, or otherwise arranged to provide one or more individual planar (which can include cylindrically planar or other flat or curved 2D surface) resonators such as can be spatially located or distributed to cover a specified spatial region or geometry (for example, along at the length of a tubular catheter or other desired object). The main line that is inductively or capacitively or hybrid coupled to the planar resonator can be used to selectively trigger or transfer power at selectively addressable different locations along the main line for use by a transducer or other load (such as can be provided in an adjacent or nearby active substrate layer), such as for example but not limited to for generating heat at the specified location of the electromagnetic-to-heat transducer load. The present techniques can be used to create or control such a spatial distribution of power output along the main line of the planar resonator using the frequency of the RF or other applied AC electromagnetic input signal for providing such controllable addressing of a specified location of a resonator and its accompanying adjacent or otherwise co-located transducer along the main line.

The present techniques can include providing a fixed-frequency planar resonator (e.g., having a characteristic resonance frequency) that can be configured to act as a frequency-dependent RF cavity. An input control signal, such as an applied AC electromagnetic input signal, can be frequency-scanned scanned, such as may be observed along the main line, and can produce what may appear or look like an amplitude dip, as seen from the main-line's perspective, at the characteristic resonance frequency of the planar resonator. Such an apparent amplitude dip is not primarily due to loss of power, but instead, is due largely to redirection of energy of the AC electrical input signal on the main-line into the planar resonator cavity at the appropriate characteristic resonance frequency of the planar resonator. In this way, a frequency-specific path can be created, such as for depositing energy at a desired location along the length of the main line at which a particular planar resonator is coupled to the main line. Such deposited energy can be transferred to a corresponding transducer that is adjacent to or otherwise co-located with the particular planar resonator being addressed and energized, thereby allowing use of the planar resonator as a control device for addressing and energizing the accompanying transducer. Without being bound by theory, an electrical or magnetic standing wave can be created in the planar resonator when the input signal frequency matches the pre-specified characteristic resonance frequency of the particular resonator. At such resonance frequency, a standing wave occurs in the electrode provided by the planar resonator line and an accompanying substrate phenomenon occurs in the adjacent or nearby active substrate, which can act as an electromagnetic-to-heat, electromagnetic-to-vibration, or other transducer. In this way, energy can be deposited into transducer provided by the substrate, such as for heat generation by the transducer, as opposed to merely draining the electrical energy out of the resonator by shunting electrical current to ground.

Multiple planar resonators having various different characteristic resonance frequencies can be arranged along and connected or coupled to the main line. Of these multiple planar resonators, only those resonators having a characteristic resonance frequency that matches an input frequency of the AC electromagnetic input signal present on the main line will resonate, thereby causing the amplitude dip (from the main line perspective) for depositing energy at the desired one or more locations of only such one or more resonating planar resonators. Other off-resonance planar resonators attached or coupled to the main line having different characteristic resonance frequencies will reflect the applied electromagnetic signal, without depositing energy (or depositing substantially less energy) at the locations of such non-resonating planar resonators. In sum, using multiple planar resonators attached or coupled to a shared main line, multiple frequency-selectable transducers or other energy deposition locations can be provided and selectively addressed by selecting the appropriate tuning frequency of the AC electromagnetic input signal placed on the main line.

Thus, the present techniques can enable the control of an energy flow path of an RF or other AC electromagnetic signal along a main line. Such control can be provided by selecting or altering the frequency of the input RF or other AC electromagnetic input signal. In the case of a planar resonator that is inductively coupled to the main line via a tap line, the amount of energy delivered can be impacted or managed by at least two factors: (1) an impedance of the connection between the main line and the planar resonator; and (2) the location of the connection or coupling into the planar resonator, which can alter the distribution of energy within the planar resonator, such as explained herein.

Figure 7:
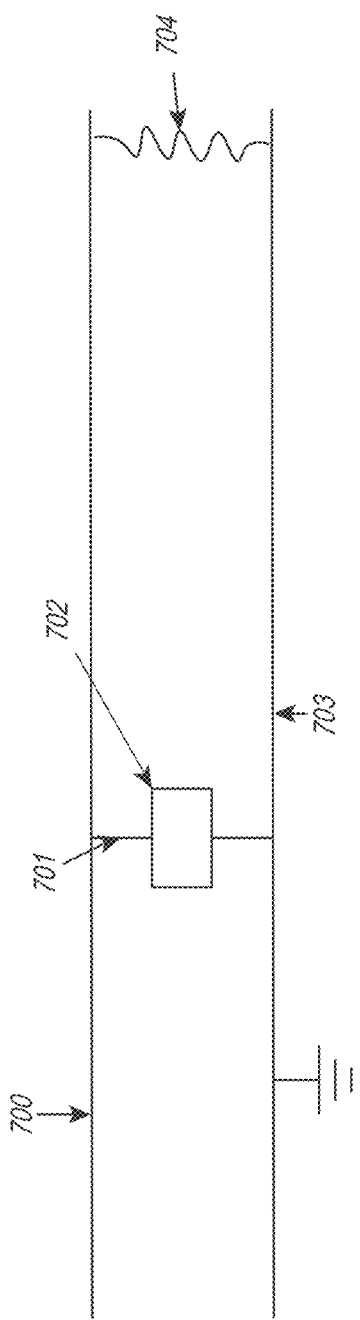
FIG. 7 shows a block diagram electrical schematic diagram of an example of an overall setup of portions of a planar resonator configuration.

FIG. 7 shows a block diagram electrical schematic diagram of an example of an overall setup of portions of a planar resonator configuration. In the example of FIG. 7, an electrically conductive main line 700 can be electrically connected or inductively coupled, such as via a tap line 701 (or via a capacitive or hybrid coupler), to a fixed characteristic resonance frequency planar resonator line 702 and to a ground line 703. One or more fixed characteristic resonance frequency planar resonator lines 702 can similarly be connected or coupled in parallel via corresponding tap lines 701 (or via corresponding capacitive or hybrid couplers) in a similar manner, such as at different physical locations along the main line 700. FIG. 7 shows conceptual representation of resistive or other load 704 between the ground line 703 and the main line 700, such as a shunt in parallel with the one or more planar resonator lines 702. The resistive load 704 need not be a separate physical component that is included; instead, the resistive load 704 is intended to represent conceptually via a shunt resistor how power can be coupled into the adjacent or nearby transducer in the substrate at resonance by a corresponding co-located particular planar resonator having a planar resonator line 702. Thus, even though the resistive load 704 is drawn in the schematic of FIG. 7 as being spaced-apart from the planar resonator line 702, such resistive load 704 can represent the load impedance of a corresponding electromagnetic-to-heat or other transducer in the substrate immediately below or adjacent to the planar resonator line 702.

Figure 8:
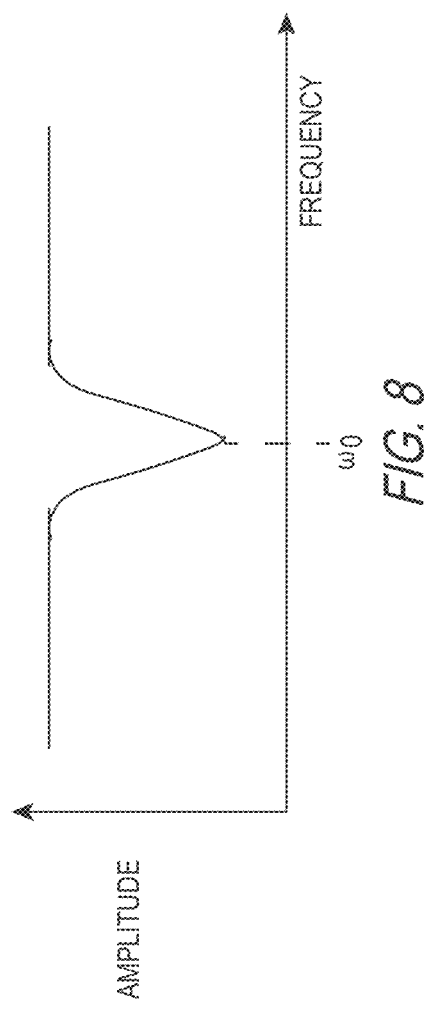
FIG. 8 shows a conceptualized (not real data) example of a graph of amplitude vs. angular frequency, w.

FIG. 8 shows a conceptualized (not real data) example of a graph of amplitude vs. angular frequency, $\omega$, showing an illustrative conceptual example of a signal amplitude dip (from the perspective of the main line) of the AC electromagnetic input signal at a specified or pre-designed response or characteristic resonance frequency, $\omega_0$, of the planar resonator having a planar resonator line 702 as shown in FIG. 7.

Figure 9:
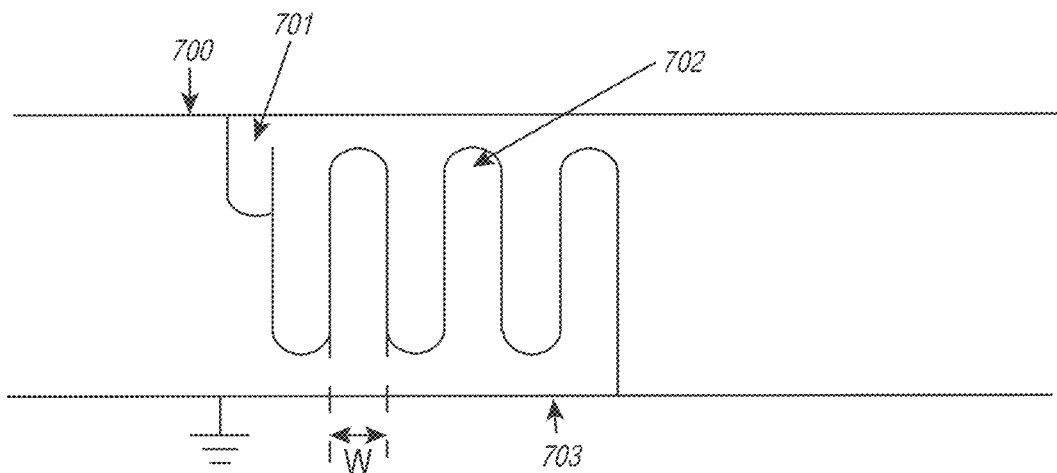
FIG. 9 shows an illustrative physical layout schematic example of a grounded planar resonator having an electrically conductive planar resonator line.

FIG. 9 shows an illustrative physical layout schematic example of a grounded planar resonator having an electrically conductive planar resonator line 702. In the example of FIG. 9, an electrically conductive main line 700 is connected to the planar resonator line 702 such as via the tap-line 701 (or via a capacitive or hybrid coupler). In this example, the planar resonator line 702 includes specified number of electrically conductive segments that can be interconnected, for example such as shown, and arranged in a serpentine, undulating, or meandering manner. In this grounded configuration of FIG. 9, the total planar resonator line 702 length (e.g., sum of segment lengths plus lengths of interconnections between such segments) can correspond to a specified multiple of quarter wavelengths ($\lambda/4$) of a desired addressing frequency of an AC electromagnetic input signal that will be used to address and energize the planar resonator having the planar resonator line 702, such as to address and energize a corresponding electromagnetic-to-heat transducer provided by an adjacent substrate, such as to create heat at the location of the transducer corresponding to the specified planar resonator when it is addressed by the appropriate frequency of the AC electromagnetic input signal on the main line 700. The physical spacing between neighboring resonator line segments within the serpentine arrangement of the planar resonator line 702 can generally be set to reduce, minimize, or eliminate electromagnetic coupling between such neighboring line segments. In general, this inter-segment spacing, W, can be about 3 to 5 times the physical linewidth of the signal trace of the planar resonator line 702. If a band of characteristic resonance or response frequencies is desired, carefully managed inter-segment spacing and coupling can be used to expand the characteristic resonant frequency range of the planar resonator line 702. This can be accomplished, for example, by decreasing the inter-segment spacing to increase inter-segment coupling within a planar resonator line 702.

Figure 10:
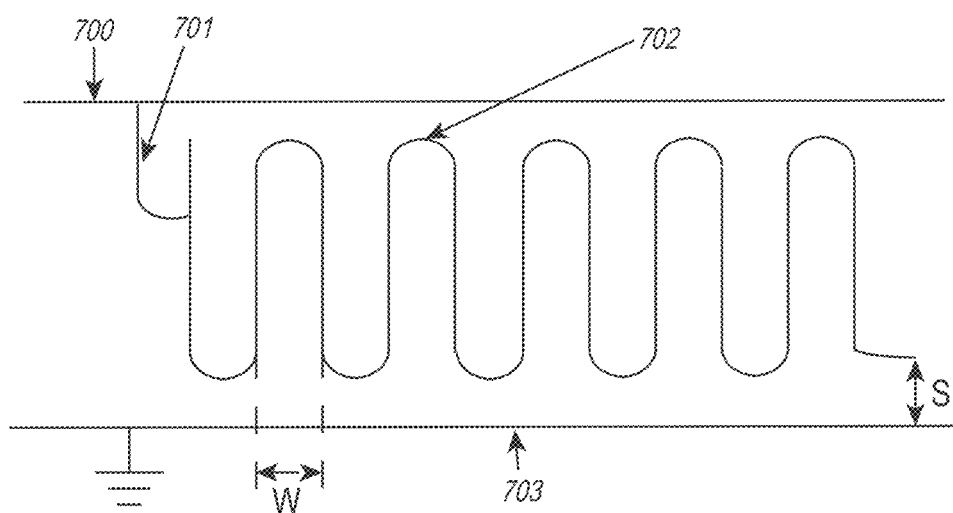
FIG. 10 shows an illustrative physical layout schematic example of a non-grounded planar resonator line.

FIG. 10 shows an illustrative physical layout schematic example of a non-grounded planar resonator line 702, e.g., a free-floating or non-terminated planar resonator line 702. In the example of FIG. 10, the main line 700 can be electrically connected to the planar resonator line 702 via the tap-line 701 (or via a capacitive or hybrid coupler), but the planar resonator line 702 is not electrically connected to the ground line 703. Instead, the planar resonator line 702 can be directed away from the ground line 703, such as to maintain a safe or desired spacing, S, therebetween, such as to help inhibit or prevent electromagnetic coupling between the planar resonator line 702 and the ground line 703.

In this example of FIG. 10, the planar resonator line 702 includes specified number of electrically conductive segments that can be interconnected such as shown and arranged in a serpentine, undulating, or meandering manner.

In this non-grounded configuration, the total planar resonator line 702 length (e.g., sum of segment lengths plus interconnections between segments) can correspond to a specified multiple of half wavelengths (λ/2) of a desired addressing frequency of an input electromagnetic signal that will be used to address the planar resonator line 702 of FIG. 10, such as to deposit heat via an electromagnetic-to-heat transducer in the adjacent substrate at the location of the specified planar resonator line 702 when it is addressed by the appropriate frequency AC electromagnetic input signal on the main line 700. The spacing between neighboring resonator line segments within the serpentine arrangement of the planar resonator line 702 can generally be set to reduce, minimize, or eliminate electromagnetic coupling between such segments, or to expand characteristic resonance frequency range, such as explained above with respect to FIG. 9.

Figure 11A:
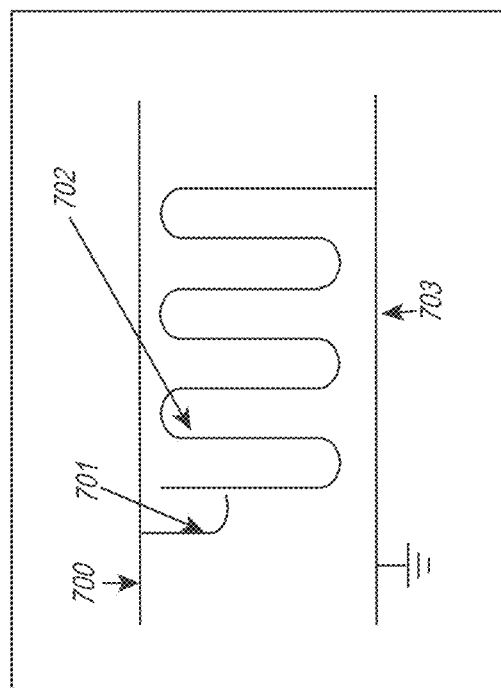
FIG. 11A (flattened planarized top physical view) and FIG. 11B (flattened planarized cross-sectional side view) shows an example of a grounded cylindrically coplanar arrangement of a planar resonator system.
Figure 11B:
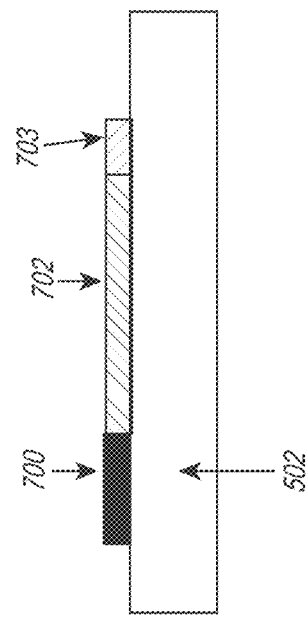

FIG. 11A (flattened planarized top physical view) and FIG. 11B (flattened planarized cross-sectional side view) shows an example of a grounded cylindrically coplanar arrangement of a planar resonator system. FIG. 11A is similar to FIG. 9. FIG. 11B provides a flattened planarized cross-sectional side view that shows an example of how the various components of the planar resonator system (e.g., including the planar resonator line 702, the main line 700, and the ground line 703) can be located on or near a surface of an active (e.g., semiconductor or other lossy dielectric) substrate 502, such as within a shared plane in a co-planar (or cylindrically co-planar) arrangement, such as within an electrode or power layer 503 that can be located adjacent or near to the active substrate 502 layer. The region of the active substrate 502 immediately below the corresponding co-located planar resonator line 702 can provide an electromagnetic-to-heat transducer that is addressable and energizable to generate heat when the corresponding planar resonator line 702 is addressed and energized. Additionally or alternatively, the region of the active substrate 502 (which can optionally be configured to include a piezoelectric property) immediately below the corresponding co-located planar resonator line 702 can provide an electromagnetic-to-vibration transducer that is addressable and energizable to generate vibration when the corresponding planar resonator line 702 is addressed and energized.

Figure 12B:
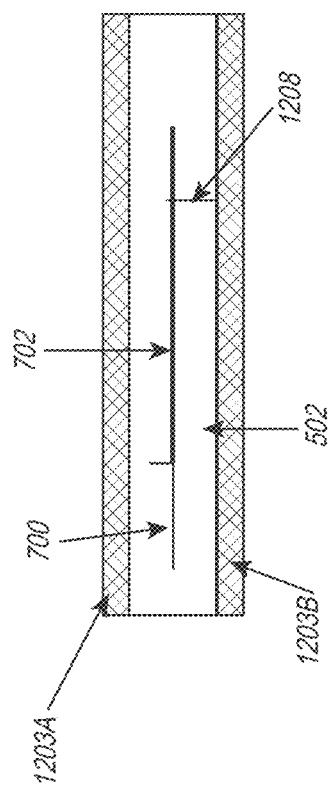
FIG. 12A (flattened planarized top physical view), FIG. 12B (flattened planarized cross-sectional side view along a first edge of FIG. 12A), and FIG. 12C (flattened planarized cross-sectional side view along a second edge of FIG. 12A) show examples of a cylindrically coplanar arrangement of the planar resonator line in a strip line arrangement.
Figure 12C:
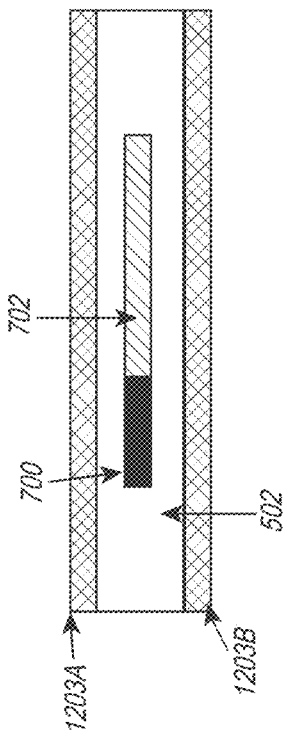
Figure 12A:
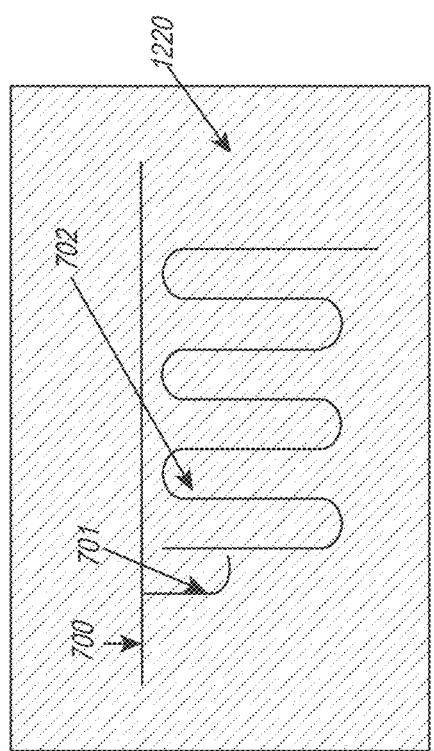

FIG. 12A (flattened planarized top physical view), FIG. 12B (flattened planarized cross-sectional side view along edge 1210 of FIG. 12A), and FIG. 12C (flattened planarized cross-sectional side view along edge 1220 of FIG. 12A) show examples of a cylindrically coplanar arrangement of the planar resonator line in a strip line arrangement. No ground line 703 is shown in FIG. 12A, but FIGS. 12B and 12C shows the ground planes 1203A-B respectively above and below the planar resonator line 702, which is located or embedded in an active substrate 502 (providing a co-located addressable and energizable electromagnetic-to-heat transducer), which separates the planar resonator line 702 from the ground planes 1203A-B in the strip line arrangement. Optionally, in a grounded strip line arrangement, the planar resonator line 702 can be generally separated by the active substrate 502 from one or both of the ground planes 1203A-B, but the planar resonator line 702 can be selectively electrically interconnected to one or both of the ground planes 1203A-B, such as by one or more electrically conductive via 1208 structures through the active substrate 502 at one or more specified locations. It is not essential that the main line 700 and the resonator 702 be along the same horizontal plane such as shown in FIGS. 12A-C, but can be arranged along the same plane for ease of manufacturing.

Figure 13A:
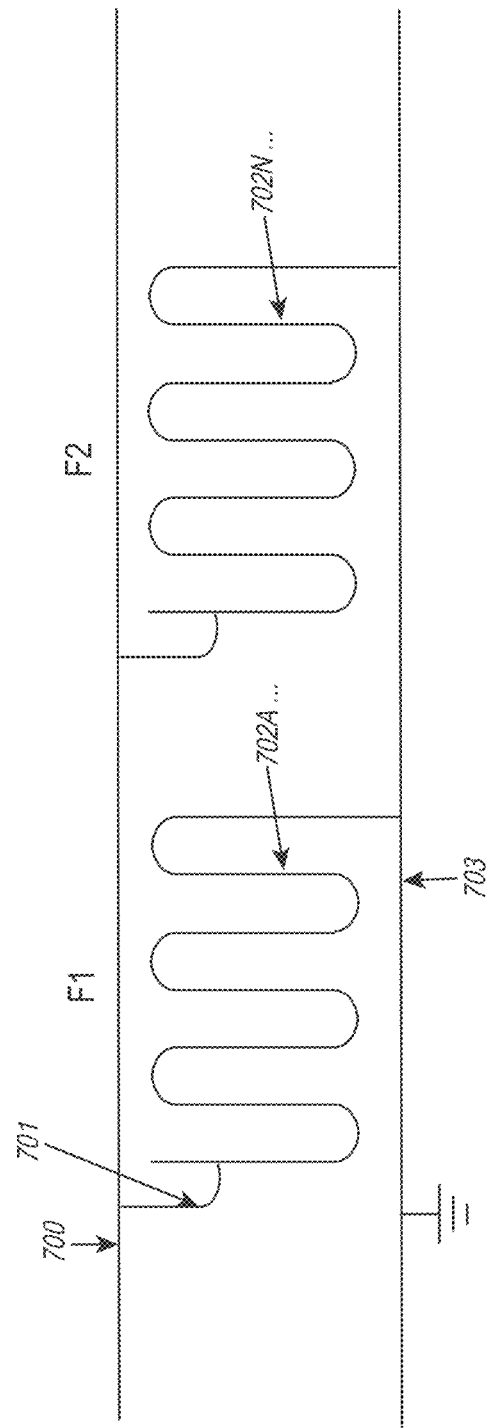
FIG. 13A (flattened planarized top physical schematic view) shows multiple (e.g., two or more) planar resonator lines at different locations along a length the main line.

FIG. 13A (flattened planarized top physical schematic view) shows multiple (e.g., two or more) planar resonator lines 702A . . . 702N at different locations along a length the main line 700. Such planar resonator lines 702A . . . 702N can be selectively addressed (e.g., individually or in one or more groups), such as selecting, adjusting, or otherwise using a frequency of an AC electromagnetic input signal that can be placed on the main line 700. The selective addressing can be performed using the planar resonator lines' 702A-N corresponding optionally different characteristic resonance frequencies $f_1$, $f_N$, such as for generating heat deposition at pre-specifiable corresponding adjacent electromagnetic-to-heat transducer locations in an active semiconductor or other substrate 502. One or more temperature sensors can optionally be located near individual resonator lines 702A-N, such as to allow readout of temperature data (and sensor identity (ID)) information indicative of the particular location of the particular temperature sensor providing the temperature reading. Such distributed temperature sensors can be accessed using electrical interconnection lines 304A-B. Such temperature information can be used to control a frequency sweep of an applied AC electromagnetic input signal selectively activating one or more particular planar resonators in a matrix of such planar resonators sharing the same main line 700. If a heat gradient is desired, for example between transducers associated with adjacent planar resonators, such adjacent planar resonators can be triggered by passing an AC electromagnetic input signal having frequency components at the different resonance frequencies of the adjacent planar resonators desired to be addressed to dynamically trigger heat generation in the corresponding electromagnetic-to-heat transducers in the adjacent or nearby active substrate.

An illustrative example can be provided as follows, with the understanding that the wavelength values given below correspond to wavelengths in free space, since the example is intended to be generic to the specific active substrate that is chosen. In practice, the resulting wavelength values should be modified depending on the permittivity of the active substrate material that is used, or depending on a composite permittivity of the active substrate material that is used in combination with a permittivity of an operating environment in which the device is being used. For example, in a strip-line configuration, wavelength in the active substrate $\lambda_s = \lambda_o / \sqrt{\epsilon_r}$, where $\lambda_o$ is the wavelength in free space and $\epsilon_r$ is the relative permittivity of the active substrate material. In a coplanar configuration, wavelength in the active substrate $\lambda_s = \lambda_o / (2 \ast \sqrt{\epsilon_{\mathit{eff}}})$ where $\lambda_o$ is the wavelength in free space and $\epsilon_{\mathit{eff}} = (\epsilon + 1)/2$, where $\epsilon\_\mathit{eff} = (\epsilon\_r + 1)/2$, where $\epsilon_r$ is the relative permittivity of the active substrate material, or preferably, where $\epsilon_r$ is the composite relative permittivity of the active substrate material in combination with a permittivity of an operating environment (e.g., tissue or blood, in an illustrative example of an intravascular device application) in which the device is used.

With this caveat in mind, continuing with the illustrative example, to selectively address a particular resonator line 702A when the frequency of the AC electromagnetic input signal on the main line 700 is 10 GHz, which has a corresponding (free space) wavelength of approximately 3 cm, the corresponding quarter wavelength (λ/4) for a grounded planar resonator line 702A is about 7.5 mm, and the corresponding half wavelength (λ/2) for a non-grounded planar resonator line 702A is 15 mm. In an illustrative catheter application example in which the catheter circumference is 4.17 mm, a quarter wavelength (λ/4) for a grounded planar resonator line 702A is less than two circumferential turns about the catheter, and the corresponding half wavelength ($\lambda/2$) for a non-grounded planar resonator line 702A is less than four circumferential turns about the catheter. For an electrical trace of the planar resonator line 702 having a line width of 0.2 mm, for example, spacing between adjacent planar resonator line segments should be at least approximately two to five times the line width for an illustrative example of a semiconductor active substrate, e.g., 1.8 mm (as an illustrative example) to avoid intercoupling between adjacent resonator line segments while allowing closer packing of planar resonator lines 702A, . . . , 702N upon the catheter structure. In an illustrative example, this means that there can be about 5 such frequency-controllable resonator addressed and energized substrate transducer heat sources per centimeter of catheter length. For example, within a 10 centimeter catheter length, there can be about 50 frequency-addressable and frequency-energizable resonator-controlled substrate transducer heat sources.

Thus, for a grounded planar resonator line 702A, the aggregate length of the serpentine, meandering, or other electrically conductive trace of the planar resonator line 702A can be 7.5 mm to permit that particular planar resonator 702A to be selectively addressed and energized using a 10 GHz frequency of an AC electromagnetic input signal applied on the main line 700, to which the planar resonator line 702A can be electrically interconnected using a corresponding individual tap-line (or capacitive or hybrid coupler) of a desired impedance. The meandering planar resonator line 702A terminates at the ground line 703. In the present case a meandering planar resonator line 702A is merely an example. The geometry or layout of the planar resonator line can depend on the space and needs of each individual application. In this way, in this grounded resonator example, a 10 GHz input signal will now resonate with this grounded resonator line 702A and will result in a power flow into the selected planar resonator line 702A.

It is possible that under the grounded planar resonator line scenario the E (electrical) wave is drained out of the resonator. This is especially true in the capacitive coupled case of the transmission line planar resonator. However, the M (magnetic) wave is trapped and will couple energy into the adjacent substrate electromagnetic-to-heat transducer to create heat.

It can be desirable to reduce or avoid any inter-segment signal coupling within a particular meandering trace planar resonator line 702A-N, such as to help establish a "crisp," e.g., highly selective, frequency response of a particular planar resonator line 702 to the applied AC electromagnetic input signal frequency. By providing an inter-segment line spacing of 3 to 5 times the line width of the serpentine or meandering electrical conductor trace of a planar resonator line 702, such inter-segment coupling can be reduced or avoided. However, if for a particular application it is desired that a particular planar resonator line 702A-N be selectively addressable using a broader range of frequencies, instead of a highly-selective narrowband or single frequency per selected resonator power flow path, careful selection and arrangement of inter-segment spacing to provide a desired amount of inter-segment coupling can help broaden the resonance frequency band of the particular planar resonator line 702A-N. Parasitic coupling may create undesirable or unpredictable results and thus may be unsuitable for or may limit reliable power flow path selection. A higher addressing frequency corresponds to lower addressing wavelength. A lower addressing wavelength decreases the corresponding aggregate trace length of the resonator lines 702A-N and, therefore, can result in less space needed or better density of the resonator lines 702A-N along the main line 700.

In certain examples, a planar resonator cavity can be capacitively coupled instead of electrically connected and inductively coupled to the main line via a tap line, which may form an inductive connection to the main line. Illustrative examples of capacitive loading are shown in FIGS. 13B, 13C, 13D, and 13E.

FIG. 13B shows a physical top view of an example illustrating how a resonant cavity can be capacitively coupled to a main line. For example, a planar resonator line 702 can be separated from the corresponding main line 700 by a gap, G, at a resonator location, rather than being electrically connected thereto by a tap-line. The resonance frequency of the capacitively coupled resonator structure can be established as described above for the electrically-connected resonator structure (e.g., 10 GHz resonance frequency corresponds to quarter wavelength ($\lambda/4$) for a grounded planar resonator 702A of about 7.5 mm). However, for a capacitively-coupled resonator structure, the distance of the gap G needed for capacitive coupling to the resonator structure is also frequency dependent, and can be determined as explained in the above-incorporated A. Gopinath and C. Gupta, "Capacitance Parameters of Discontinuities in Microstriplines," IEEE Trans. On Microwave Theory and Techniques, Vol. MTT-26, No. 10, October 1978, p. 831-836. Thus, by selecting the appropriate resonator (aggregate planar resonator line 702 length, meandering spacing W, etc.) and the appropriate capacitive coupling gap, G, the resonator can be activated (e.g., addressed and energized) at a specified characteristic resonance frequency of the resonator using an appropriately selected frequency of an applied AC electromagnetic input signal applied to a main-line 700 that is electrically insulated from the planar resonator line 702 at the capacitive coupling gap, G. This can enable frequency-controlled deposition of heat using an electromagnetic-to-heat transducer provided by an adjacent semiconductor or other active heating substrate at desired locations of one or more appropriately tuned resonator cavities. Other resonators, which can similarly be capacitively coupled to the main line at one or more other (different) resonance frequencies can be configured to reflect, at the selected resonance frequency, energy of the electrical signal applied on the main-line. In this way, only the one or more desired capacitively coupled resonators being addressed are selectively activated.

FIG. 13C shows a top view of an example of a serpentine or meandering resonant cavity electrically conductive trace of a planar resonator line 702 that can be capacitively coupled to a main line 700 by an insulating gap, G, at a desired capacitive coupling location. At other locations, the resonator structure can be separated from the main line by a larger insulating separation spacing, I, e.g., I>G. In this way, the insulating gap G dominantly determines capacitive coupling of the planar resonator line 702 structure to the main line 700, rather than the other locations of the planar resonator line 702 structure, which have the larger separation, I, from the main line 700 and, therefore, such other locations of the planar resonator line 702 structure are not capacitively coupled to the main line 700.

Figure 13D:
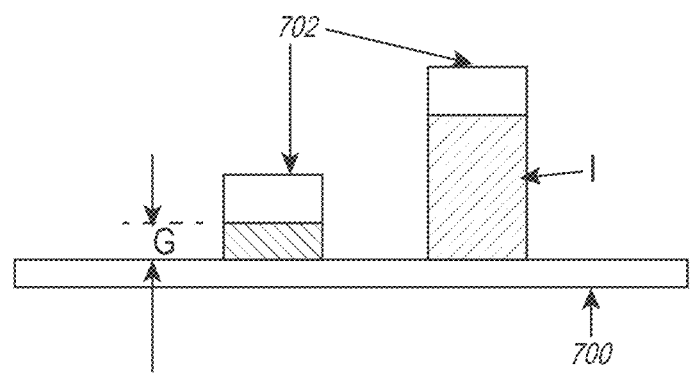

FIG. 13D shows a side view of an example in which a specific portion of a capacitively coupled planar resonance line structure can be separated from a main line by an insulating gap, G, such as to capacitively couple the planar resonator line 702 structure to the main line 700, while other portions of the capacitively coupled planar resonator line 702 structure can be separated from the main line 700 by a larger insulating separation spacing, I, such that such other portions of the planar resonator line 702 structure do not capacitively couple to the main line 700.

Figure 13E:
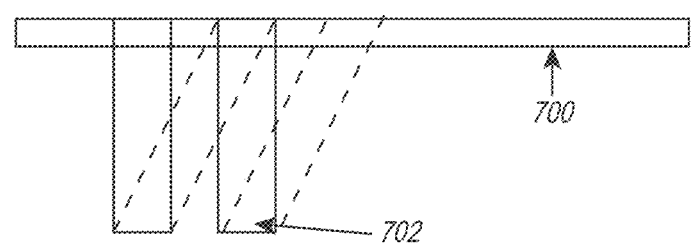

FIG. 13E shows an example of a capacitively coupled planar resonator line 702 structure that can be wrapped around a main line 700, such as a desired location that can be separated from the main line 700 by an insulating gap G that dominantly determines the capacitive coupling of the planar resonator line 702 structure to the main line 700, with other portions of the planar resonator line 702 structure separated from the main line 700 by a larger insulated distance, I, such as not to capacitively couple such other locations of the planar resonator line 702 structure to the main line 700.

As an example, a physical device in which planar resonator lines 702 with correspondingly located substrate transducer heat sources can be arranged along a main line is a catheter. The transducer heat sources can be controlled by their corresponding resonators, in response to an applied AC electromagnetic input signal, and used to provide heat to inhibit biofilm or sterilize the catheter. A set of planar resonator line 702 controlled transducer heat sources can be arranged along a main line 700 and the applied AC electromagnetic input signal placed on the main line 700 can be programmed to effectively controllably address and energize a matrix of substrate transducer heat sources corresponding to respective resonators, associated thermal gradients can enable a desired effect of thermal energy either directly on the physical device such as a catheter or onto surrounding material though heat conduction from the device to the material.

Figure 1B:
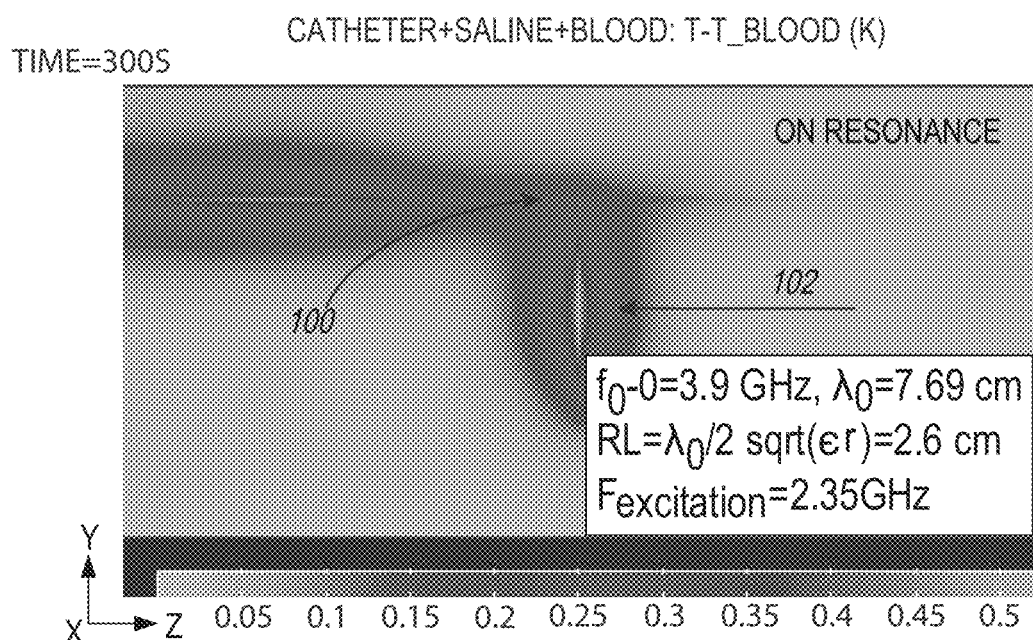

FIG. 1 shows computer-simulation results of on and off resonance temperature field after power is supplied to a computer-modeled main line coupled to a computer-modeled planar resonator coupled to a computer-modeled transducer in an adjacent substrate. The resonator 102 operating "on resonance" at an applied AC electromagnetic input signal frequency of 2.35 GHz has significantly higher temperature then the resonator operating "off resonance" at an applied AC electromagnetic input signal frequency of 3.9 GHz. The resonators are modeled as being capacitively coupled to the main-line. The resonator is modeled as being located in the middle of a catheter having wall of thickness 0.5 mm with a modeled layer of blood and saline on either side, each at a modeled thickness of 0.6 mm.

Figure 2:
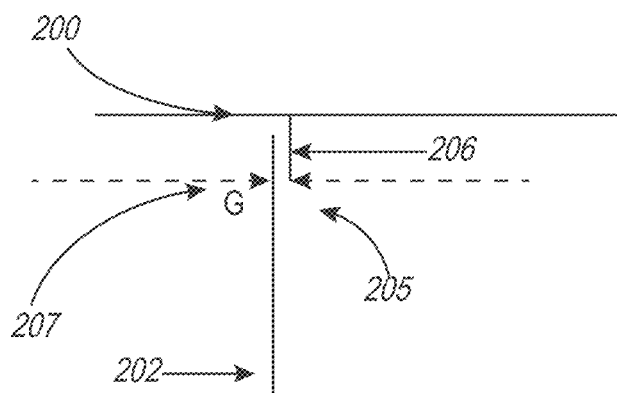
FIG. 2 shows an example of a planar resonator line that can include a hybrid coupler arranged between a main line and a planar resonator line.

FIG. 2 shows an example of a schematic of a planar resonator line 202 that can include a hybrid coupler 205 arranged between a main line 200 and a planar resonator line 202. In this example, the hybrid coupler 205 can include an inductive tap-line 206, such as can extend as a stub from the main line 200 at a particular location of a planar resonator line 201. The hybrid coupler 205 can also include, e.g., in series with the inductive tap-line 206, a capacitive coupler 207, shown with a capacitive spacing G, that can be arranged between the inductive tap-line 206 and the planar resonator line 202. In an example of such a hybrid coupler 205 arrangement, both the inductance of the tap-line 206 and the capacitance of the capacitive coupler 207 can be used to transfer power from the main-line to the planar resonator line 201. Such a combination of inductive and capacitive components provide flexibility in determining the capacitive spacing and thus can help enable use of a variety of manufacturing processes.

Figure 3:
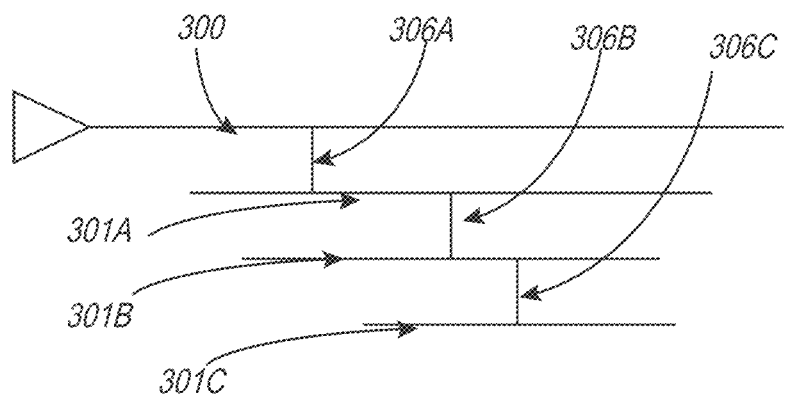
FIG. 3 shows an example of a series cascade arrangement of planar resonators.

FIG. 3 shows an example of a series cascade arrangement of planar resonators 301A, . . . , 301C that can be arranged between a commonly shared main line 300. In this illustrative example, the individual planar resonators 301A, . . . , 301C can respectively include an inductively coupled tap line 306A, . . . , 306C, which can be inductively coupled to the main-line 300 (for the first planar resonator 301 in the series cascade) or to a preceding planar resonator for succeeding planar resonators in the series cascade arrangement.

Figure 4A:
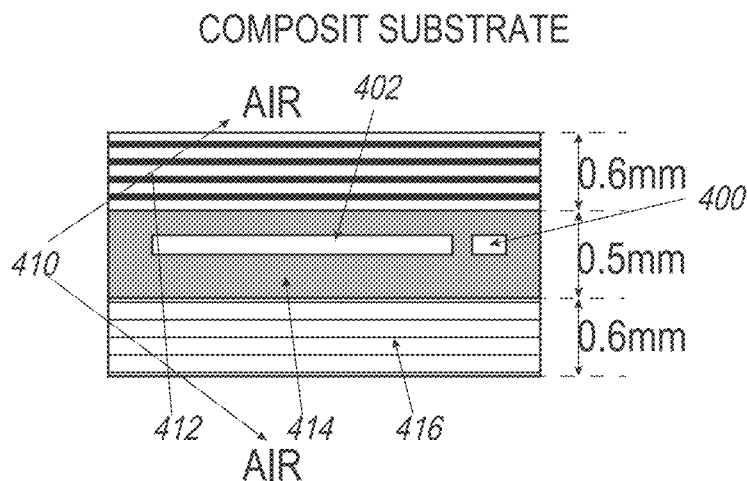
FIG. 4A shows an example of a modeled arrangement of a planar resonator in an application in which the planar resonator is embedded together with a main-line within a thick catheter.

FIG. 4A shows an example of a modeled arrangement of a planar resonator 401 in an application in which the planar resonator 401 is embedded together with a main-line 400 within a 0.5 mm thick catheter 414 made from a biocompatible polymeric material. The planar resonator 401 is present together with an adjacent active (e.g., semiconductor or other lossy dielectric) substrate electromagnetic-to-heat transducer (which is not explicitly separately shown in FIG. 4A). A 0.6 mm thick region of blood 412 is modeled as being located above the catheter 414. A 0.6 mm thick region of saline 416 is modeled as being located immediately below the catheter 414. Together, the blood 412 and saline 416 model an example of an operating environment of the catheter 414 and its embedded planar resonator 401.

Figure 4B:
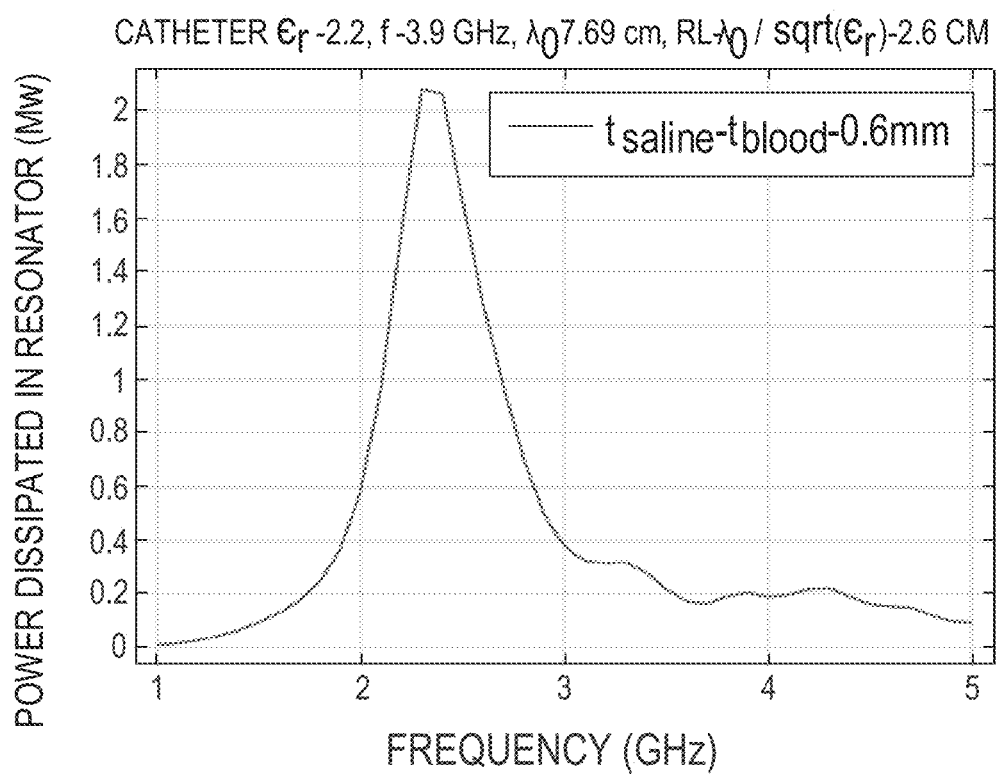
FIG. 4B shows a corresponding computer-modeled graph of frequency response of power dissipated in the resonator as a function of frequency of an AC electromagnetic input signal applied to the main line, for the arrangement of FIG. 4A.

FIG. 4B shows a corresponding computer-modeled graph of frequency response of power dissipated in the resonator 401 as a function of frequency of an AC electromagnetic input signal applied to the main line 400, for the arrangement of FIG. 4A. From FIG. 4B it is seen that the characteristic resonance frequency of about 2.3 GHz is below the expected resonance frequency of 3.9 GHz for the resonator modeled using only the permittivity of the catheter 414, without accounting for the compositive permittivity that includes the permittivity contributions of the operating environment (here, modeled as blood and saline). In FIG. 4B, the computer-modeled power dissipation of the resonator at the characteristic resonance frequency is about 2 mW.

Figure 5A:
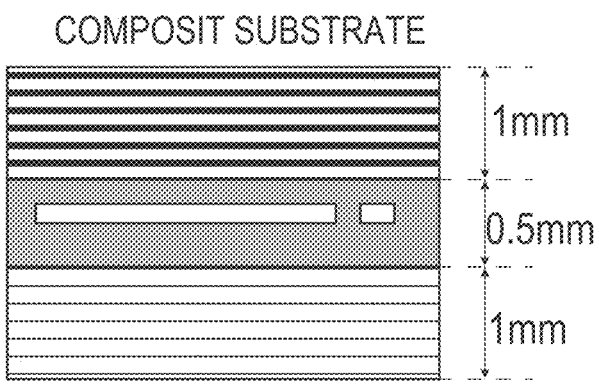
FIG. 5A is an example of an arrangement similar to that shown in FIG. 4A, but in which the thickness of the blood and saline regions have been extended to twice the thickness of such regions as shown in FIG. 5A.
Figure 5B:
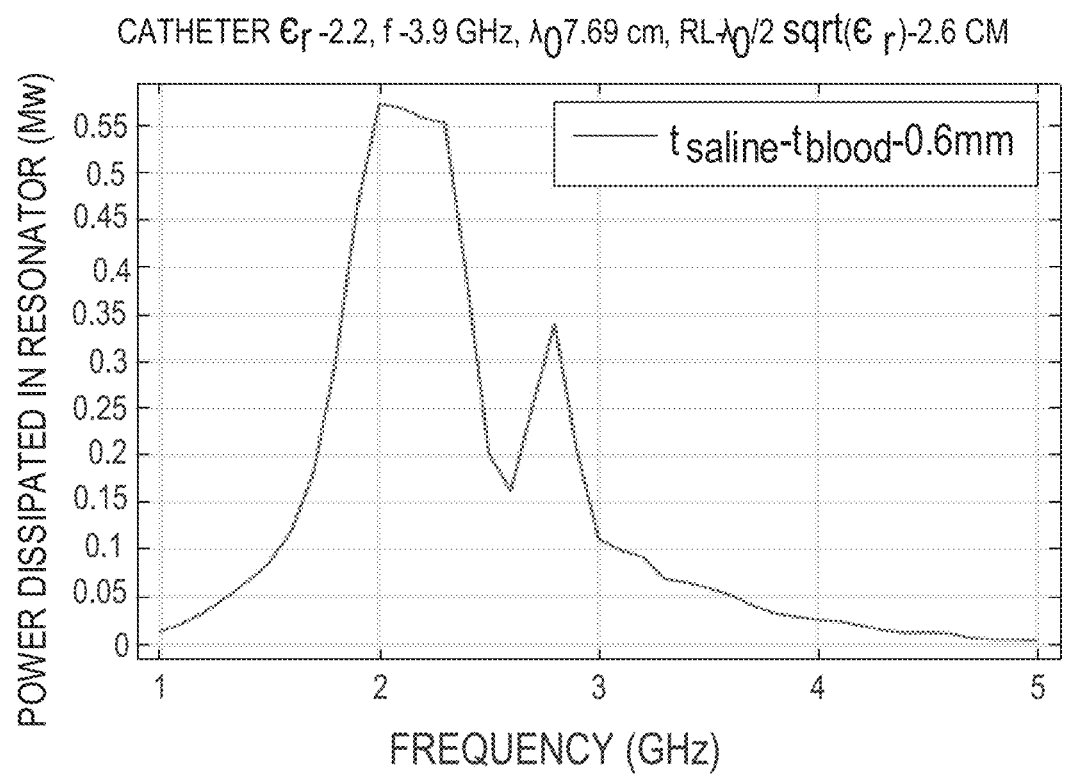
FIG. 5B shows a resulting computer modeled graph, similar to that of FIG. 4B, but corresponding to the arrangement shown in FIG. 5A instead of the arrangement shown in FIG. 4A.

FIG. 5A is an example of an arrangement similar to that shown in FIG. 4A, but in which the thickness of the blood and saline regions have been extended to 1 mm, which is twice the thickness of such regions as shown in FIG. 5A. FIG. 5B shows a resulting computer modeled graph, similar to that of FIG. 4B, but corresponding to the arrangement shown in FIG. 5A instead of the arrangement shown in FIG. 4A. In FIG. 5B, it is seen that the computer-modeled characteristic resonance frequency has dropped to around 2 GHz and the computer-modeled power dissipation of the planar resonator at such characteristic resonance frequency has dropped to about 0.55 mW.

Figure 6A:
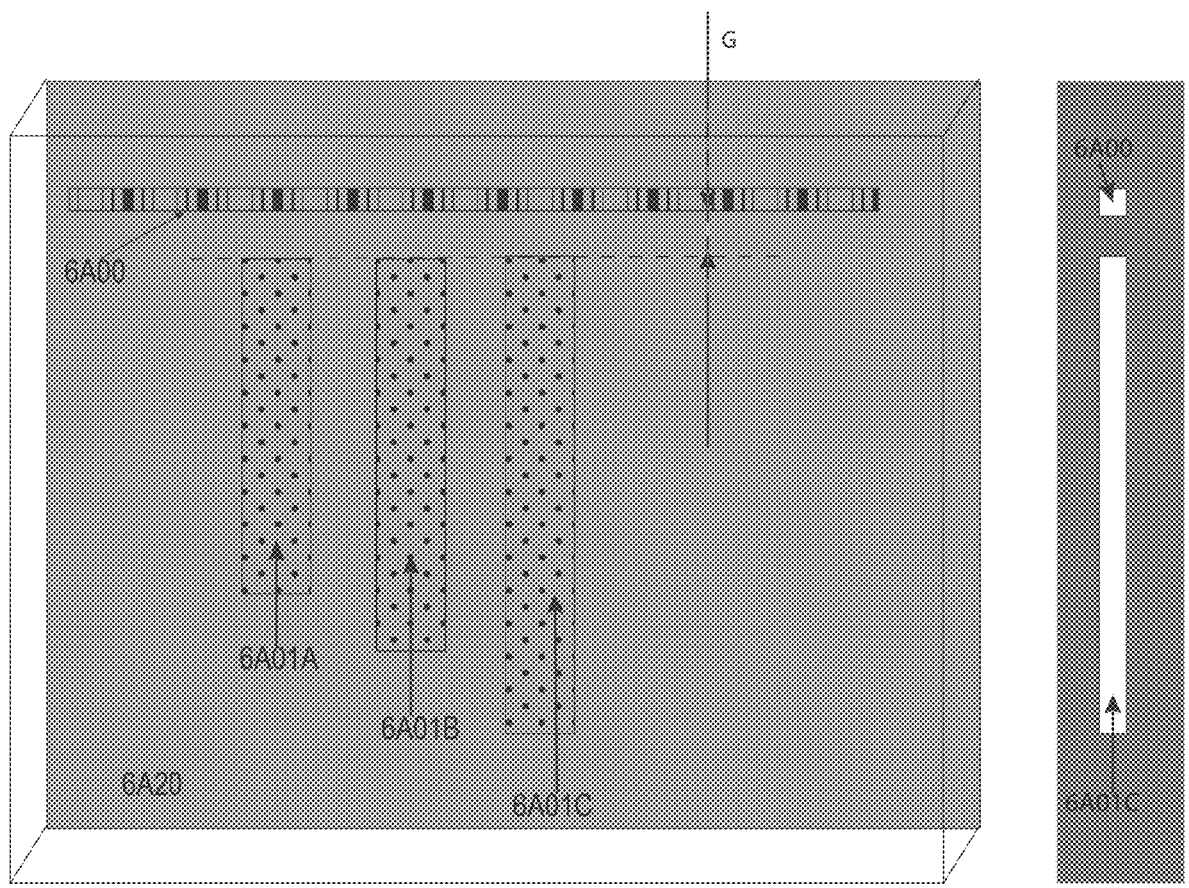
FIG. 6A is an example of a plurality of planar resonators including a main line and planar resonator lines, co-planarly located within the same plane embedded within the substrate, with a dielectric gap between the main line and the planar resonator lines to form capacitive couplers therebetween.

FIG. 6A is an example of a plurality of planar resonators including a main line 6A00 and planar resonator lines 6A01A, . . . , 6A01C, co-planarly located within the same plane embedded within the substrate 6A20, with a dielectric gap between the main line 6A00 and the planar resonator lines 6A01A, . . . , 6A01C to form capacitive couplers therebetween. In an example, regions of the substrate 6A02 immediately adjacent (e.g., above or below) the planar resonator lines 6A01A, 6A01C can be a lossy dielectric such as to provide electromagnetic-to-heat transducers in regions of the substrate adjacent to and controlled by respective planar resonator lines 6A01A, 6A01C. Other regions of the substrate 6A02, such as the regions immediately adjacent (e.g., above or below) the main line 6A00 can be less lossy than the regions of the substrate near the planar resonator lines 6A01A, . . . , 6A01C that provide electromagnetic-to-heat transducers. Using a less lossy or lossless dielectric in regions of the substrate 6A20 that are adjacent to the main line 6A00 can help avoid loss in the applied AC electromagnetic input signal as it travels down a length of the main line 6A00, which can be particularly important when such length is arranged to be long enough to accommodate a large number of planar resonators 6A01 that are capacitively or otherwise coupled to the main line 6A00.

Figure 6B:
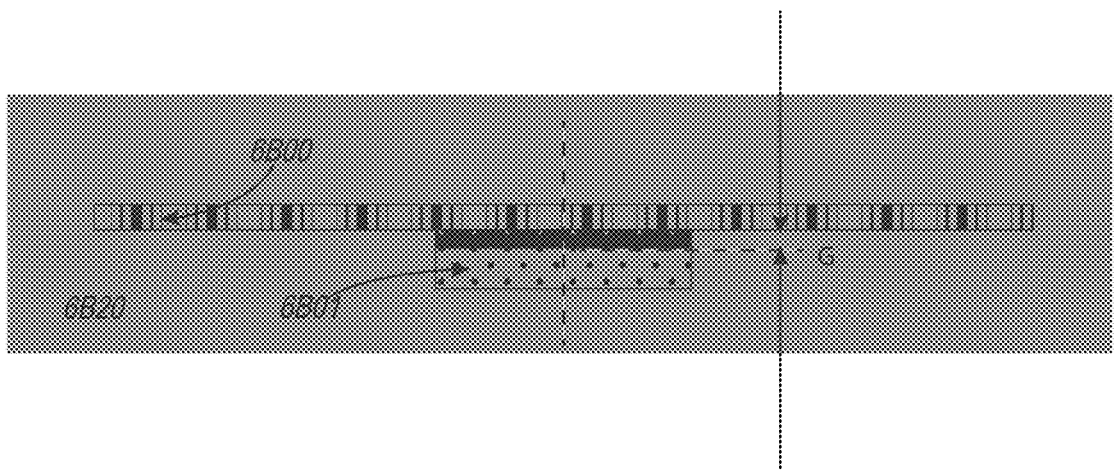
FIG. 6B is a side cross-sectional view example of a planar resonator including a main-line and a planar resonator line embedded in a substrate in different layers, rather than in a co-planar arrangement, with a gap G therebetween for capacitive coupling.

FIG. 6B is a side cross-sectional view example of a planar resonator including a main-line 6B00 and a planar resonator line 6B01 embedded in a substrate 6B20 in different layers, rather than in a co-planar arrangement, with a gap G therebetween for capacitive coupling. Again, portions of the substrate 6B20 nearby and controlled by the planar resonator line(s) 6B01 can be made more lossy, such as to provide and promote electromagnetic-to-heat transduction, while portions of the substrate 6B20 that are not as near to the planar resonator line(s) 6B01 but are instead near the main-line 6B02 or between adjacent planar resonators, can be made less lossy, such as to either promote transmission of the AC electromagnetic input signal along the length of the main line 6B00 or to avoid heating in regions between adjacent planar resonators, if desired.

Example of Sweep Operation

Figure 14A:
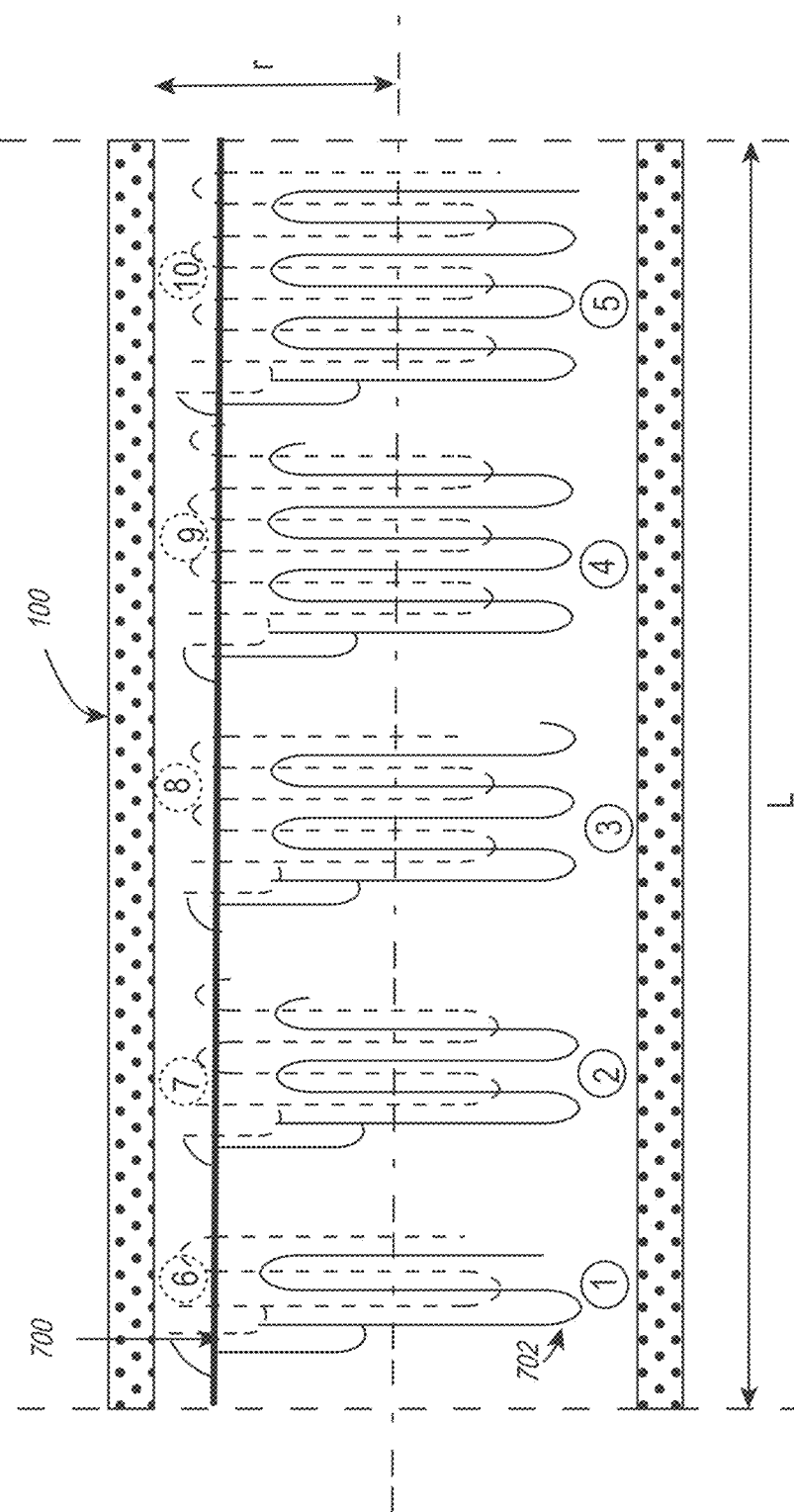
FIGS. 14A (side view) and 14B (top view of an unrolled cylindrically planar surface) show a catheter of cylindrical radius, r, including a heating zone of length, L, in which a number of planar transmission line resonators can be located, such as can be connected to a shared main line such as for applying an electrical input signal for selectively temporally actuating ones of the planar resonators.

FIGS. 14A (side view) and 14B (top view of an unrolled cylindrically planar surface) show a catheter of cylindrical radius, r, including a heating zone of length, L, in which a number of planar transmission line resonators can be located, such as can be connected to a shared main line such as for applying an electrical input signal for selectively temporally actuating ones of the planar resonators such as to address and energize a corresponding adjacent substrate transducer heat source neutralize a pathogen by dynamically creating a transducer heat source in an adjacent active substrate portion of the catheter. In this illustrative example, ten planar resonators (T1, . . . , T10) are shown, such as five planar resonators on a first side of the catheter, shown in solid lines, and another five planar resonators on an opposing second side of the catheter, shown in dashed lines.

FIG. 14C shows a simplified top view of the unrolled cylindrically planar surface of the catheter showing a grid indicating the general arrangement of the ten planar resonators (T1, . . . , T10) together with their corresponding characteristic resonance frequencies that can be used to selectively address and actuate the planar resonators T1, . . . , T10, either individually, or in groups. Different planar resonators having different characteristic resonance frequencies can optionally be concurrently addressed by a shared AC electromagnetic input signal provided on a main line to all or a group of the planar resonators, such as by including a superpositioned or other AC electrical or electromagnetic input signal having frequency components at the different resonance frequencies of the planar resonators to be concurrently addressed. Moreover, these different frequency components need not have the same power level, but can optionally be provided with different power levels at such respective frequencies.

In an illustrative, non-limiting heat sterilization application using an arrangement such as shown in FIGS. 14A-14C to treat *Staphylococcus epidermidis*, for example, effective heat sterilization will occur at a sterilization target temperature of 45° C. to 50° C. The present example can be used to maintain a specified region or heat zone at such sterilization target temperature of 45° C. to 50° C. for a cumulative time duration of 30 minutes, such as can be achieved in 60 bursts of 30 seconds each.

In an illustrative, non-limiting example, a sweep can be configured to temporally sequentially selectively activate individual ones of planar resonators in 30 second bursts. In an example, this can be carried out in a manner to effect a temperature gradient differential of 10° C. between a selected "hottest" sterilizing planar resonator and transducer region and its neighboring planar resonator and transducer regions, which can optionally also be maintained during such time periods at a heated temperature that is not quite as hot as the selected "hottest" sterilizing planar resonator and transducer region.

Before initiating the temperature activation sweep, a temperature measurement of the various locations T1, . . . , T10 on the grid can be performed, with the resulting measurements stored in memory circuitry. A safety test can then be performed to compare the measured temperatures against biological tolerance values, to ensure that when the heat sterilization sweep is initiated, the various locations T1, . . . , T10 on the grid are at temperatures that are within a specified the biological tolerance of nearby tissue. If so, temperature activation sweep of the planar resonators T1, . . . , T10 and corresponding substrate transducer heat sources on the grid can proceed.

At step 1 of the sweep, an electrical input signal with frequency components at 1.0 GHz, 2.0 GHz, and 1.1 GHz can be applied to the main line that is electrically connected or capacitively coupled to the planar resonators T1, . . . , T10. This activates the planar resonators T1, T2, and T6. The power levels of the electrical input signal components at 2.0 GHz and 1.1 GHz can be kept less than the power level of the electrical input signal component at 1.0 GHz, such as to address and energize corresponding transducers to establish or maintain a temperature of 50° C. in the active substrate transducer heat source at the planar resonator T1, while concurrently establishing or maintaining a temperature of 40° C. in the active substrate transducer heat source at the planar resonators T2, T6, with the other planar resonators T3, T4, T5, T7, T8, T9, T10 having corresponding transducers not generating any heat and, therefore, remaining at body temperature of 37° C. This state is illustrated in Table 5.

TABLE 5

Status during Step 1 (first 30 second burst) of Sweep

| T6 = 40° C. | T7 = 37° C. | T8 = 37° C. | T9 = 37° C. | T10 = 37° C. |
|---|---|---|---|---|
| T1 = 50° C. | T2 = 40° C. | T3 = 37° C. | T4 = 37° C. | T5 = 37° C. |

At step 2 of the sweep, an electrical input signal with frequency components at 1.0 GHz, 1.1 GHz, 1.2 GHz, 2.0 GHz, 2.2 GHz, and 2.4 GHz can be applied to the main line that is electrically connected or capacitively coupled to the planar resonators T1, . . . , T10. This activates the active substrate heat source transducers corresponding to the planar resonators T1, T2, T3, T6, T7, and T8. The power levels of the electrical input signal components at 1.0 GHz, 1.2 GHz, 2.0 GHz, 2.2 GHz, and 2.4 GHz GHz can be kept less than the power level of the electrical input signal component at 1.1 GHz, such as to establish or maintain a temperature of 50° C. in the active substrate transducer heat source at the planar resonator T2, while concurrently establishing or maintaining a temperature of 40° C. in the active substrate transducer heat sources at the planar resonators T1, T3, T6, T7, and T8, with the transducers corresponding to the other planar resonators T4, T5, T9, T10 not generating any heat and, therefore, remaining at body temperature of 37° C. This state is illustrated in Table 6.

TABLE 6

Status during Step 2 (second 30 second burst) of Sweep

| T6 = 40° C. | T7 = 40° C. | T8 = 40° C. | T9 = 37° C. | T10 = 37° C. |
|---|---|---|---|---|
| T1 = 40° C. | T2 = 50° C. | T3 = 40° C. | T4 = 37° C. | T5 = 37° C. |

At step 3 of the sweep, an electrical input signal with frequency components at 1.1 GHz, 1.2 GHz, 1.3 GHz, 2.2 GHz, 2.4 GHz, and 2.6 GHz can be applied to the main line that is electrically connected or capacitively coupled to the planar resonators T1, . . . , T10. This activates the transducers corresponding to the planar resonators T2, T3, T4, T7, T8, and T9. The power levels of the electrical input signal components at 1.1 GHz, 1.3 GHz, 2.2 GHz, 2.4 GHz, and 2.6 GHz can be kept less than the power level of the electrical input signal component at 1.2 GHz, such as to establish or maintain a temperature of 50° C. in the active substrate transducer at the planar resonator T3, while concurrently establishing or maintaining a temperature of 40° C. in the active substrate transducers at the planar resonators T2, T4, T7, T8, and T9, with the transducers corresponding to the other planar resonators T1, T6, T9, T10 not generating any heat and, therefore, remaining at body temperature of 37° C. This state is illustrated in Table 7.

TABLE 7

Status during Step 3 (third 30 second burst) of Sweep

| T6 = 37° C. | T7 = 40° C. | T8 = 40° C. | T9 = 40° C. | T10 = 37° C. |
|---|---|---|---|---|
| T1 = 37° C. | T2 = 40° C. | T3 = 50° C. | T4 = 40° C. | T5 = 37° C. |

The sweep can proceed in a similar manner through further steps to move the hot spot around in the grid, such as while optionally maintaining adjacent locations on the grid at a lesser elevated temperature above body temperature.

The sweep can be repeated until each location on the grid has achieved a desired sterilization temperature (e.g., 50° C.) for a cumulative time duration of 30 minutes, to neutralize the *Staphylococcus epidermidis* present in the heated zone spanned by the grid or matrix of planar resonators corresponding to transducers providing localized heat sources.

Although the above example has explained an approach to concurrently delivering different temperatures to transducers of corresponding different planar resonators in the grid/matrix by adjusting the power level of the electrical input signal components at those frequencies, additionally or alternatively, the desired frequency components can be applied with a specified relative duration or duty cycle relative to one or more other frequency components. For example, for the adjacent planar resonators that are desired to have transducers that operate at a lower temperature than the "hot spot" planar resonator in the grid, the electrical input signal can establish or maintain such frequency components for a shorter interval than the 30 second burst, or can use a pulse-width or other modulation technique to intermittently activate those planar resonators and corresponding transducers that are desired to provide heat at a lesser temperature relative to a planar resonator and transducer that is more frequently activated to achieve a higher temperature. Such modulation techniques can use closed-loop control based on a sensed or measured temperature from a temperature sensor corresponding to or located near a particular planar resonator and transducer being intermittently operated or modulated.

Phase Control of Energy Delivery to Substrate Such as to Control Power of Hotspot Additionally or alternatively, relative phase control of the applied electrical signal or signals at a particular frequency can be used to adjust the power of two (or more) planar resonators that can be located close enough to each other such that their generated electromagnetic fields can interfere with each other, e.g., constructively or destructively, such as to vary the intensity of heat delivered at a particular location associated with such interfering resonators.

Figure 15A:
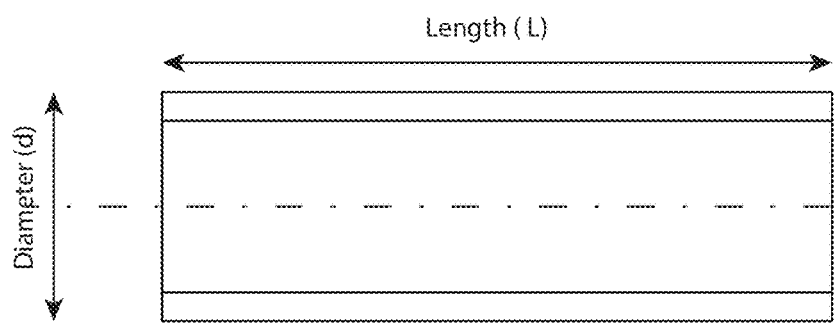
FIG. 15A shows an example of a cylindrical body (e.g., a catheter) having a heating zone.
Figure 15B:
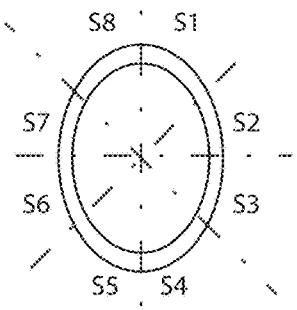
FIG. 15B shows an end view of the cylindrical body of FIG. 15A.
Figure 15C:
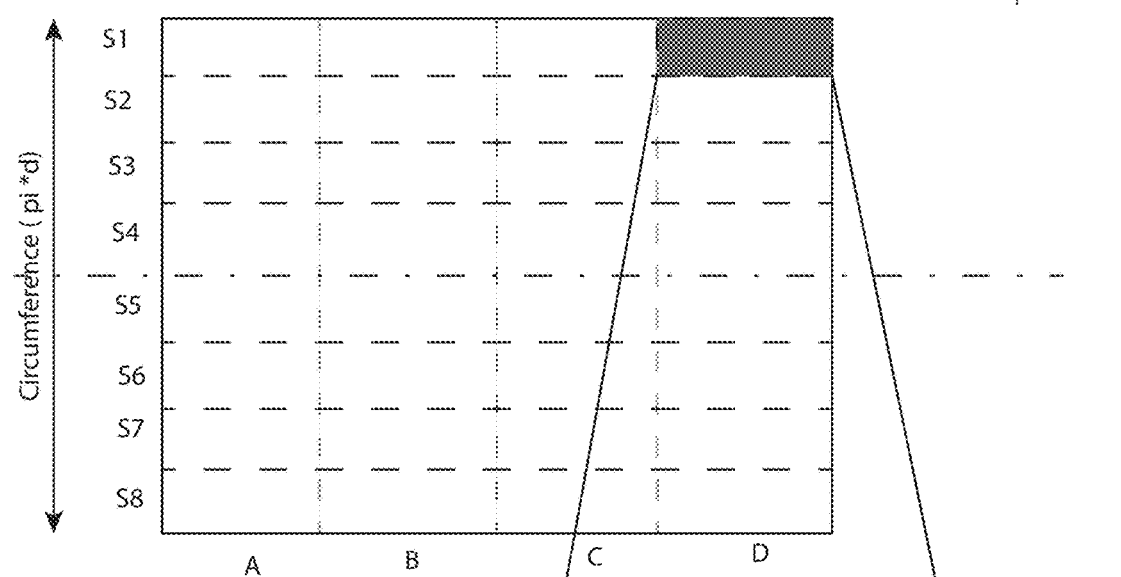
FIG. 15C shows the "unrolled" planar representation of the cylindrical body of FIG. 15A.
Figure 15D:
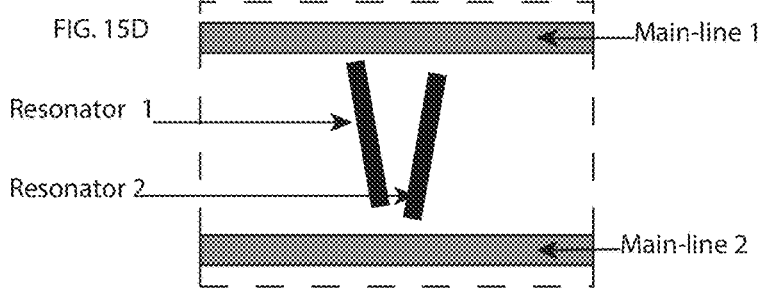
FIG. 15D shows an example of a 3D volumetric segment of the cylindrical body of FIG. 15A.

FIG. 15A shows an example of a cylindrical body (e.g., a catheter) having a heating zone of length L and having a cylindrical diameter d. FIG. 15B shows an end view of the cylindrical body of FIG. 15A, which can be angularly divided, such as with respect to its central longitudinal axis, into a desired number of volumetric sectors. In the illustrative example of FIG. 15B, the volume of the cylindrical body can be divided into 8 angular sectors, such as S1, S2, S3, S4, S5, S6, S7, and S8, such as shown in FIG. 15B. FIG. 15C shows the "unrolled" planar representation of the cylindrical body of FIG. 15A, with the angular volumetric sectors (e.g., such as S1, S2, S3, S4, S5, S6, S7, and S8) shown as horizontal rows, and further defined into a desired number of longitudinal sections (e.g., A, B, C, D), such as shown in FIG. 15C as vertical columns. FIG. 15D shows an example of a 3D volumetric segment (S1, D) defined by a particular angular sector S1 and a particular longitudinal section D.

An individual volumetric segment, such as the segment (S1, D), can include at least two resonators, such as Resonator 1 and Resonator 2 that are schematically shown in simplified form in FIG. 15D. In the segment (S1, D) shown in FIG. 15D, the two resonators, Resonator 1 and Resonator 2, can be physically located close enough to each other on or within that particular segment to permit electromagnetic interference therebetween, and which can be located far enough from other resonators in other segments to substantially avoid electromagnetic interference with such other resonators in such other nearby segments or in other more distant segments. In FIG. 15D, Resonator 1 can be selectively frequency-addressed, such as by applying an electrical signal to Main-line 1, to which Resonator 1 is shown as being closer and to which it can be capacitively coupled, the applied electrical signal having at least a frequency component at the particular addressing frequency of Resonator 1, such as explained herein. Similarly, Resonator 2 can be selectively frequency-addressed, such as by applying an electrical signal to Main-line 2, to which Resonator 2 is shown as being closer and to which it can be capacitively coupled, the applied electrical signal having at least a frequency component at the particular addressing frequency of Resonator 2, such as explained herein. In an example, Resonator 1 and Resonator 2 can be tuned to the same addressing frequency (e.g., 1.0 GHz), such that application of an electrical signal having at least a component at the same particular addressing frequency (e.g., 1.0 GHz) activates both of Resonator 1 and Resonator 2. However, the phase of the electrical signal applied on Main-line 1 can be specified or adjusted such as with respect to the phase of the electrical signal applied on Main-line 2, such as explained herein, such as to vary power delivery and heat generation using such relative phase control of the electromagnetically interfering Resonator 1 and Resonator 2.

For example, when the electrical signals are applied to Main-line 1 and Main-line 2 at the same particular addressing frequency of both of these electromagnetically interfering Resonator 1 and Resonator 2, and when such electrical signals are also applied at the same phase, such that the relative phase angle between these two applied electrical signals is 0 degrees, the resulting thermal energy produced by the combination of the selectively addressed Resonator 1 and Resonator 2 will be at a relative maximum. This is due to constructive interference between these two resonators by applying these two electrical signals at the same particular addressing frequency and at the same phase.

When the electrical signals applied to Main-line 1 and Main-line 2 at the same particular addressing frequency of both of these electromagnetically interfering Resonator 1 and Resonator 2 are out of phase, such that the relative phase angle between these two applied electrical signals is 180 degrees, the resulting thermal energy produced by the combination of Resonator 1 and Resonator 2 will be less than when these signals are in-phase. In such an example, the resulting thermal energy produced by the combination of Resonator 1 and Resonator 2 can be at a relative minimum, due to destructive interference between these two resonators by applying these two electrical signals at the same particular addressing frequency but 180 degrees out of phase with respect to each other.

When the electrical signals applied to Main-line 1 and Main-line 2 at the same particular addressing frequency of both of these electromagnetically interfering Resonator 1 and Resonator 2 are out of phase by an intermediate amount, such as by 45 degrees or by 90 degrees, for example, the resulting thermal energy produced by the combination of Resonator 1 and Resonator 2 will be in between (1) the relative maximum due to constructive interference between these resonators when the phase angle is 0 degrees and (2) the relative minimum due to destructive interference between these resonators when the phase angle is 180 degrees.

Thus, by applying respective electrical signals at the same particular addressing frequency to at least two resonators configured for being addressed using the same particular addressing frequency, where these at least two resonators are located closely enough to each other to permit electromagnetic interference effects therebetween, the power delivered to the adjacent location of the lossy substrate and the resulting heat generated at that adjacent location of the lossy substrate, can be specified or adjusted by specifying the relative phase angle of the particular electrical signal applied to the particular main-line used to address each individual resonator. These two resonators that can be configured to be located closely enough to each other to permit electromagnetic interference between such resonators can also be configured to be physically located far enough from other resonators (e.g., such as from other resonators located and associated with other segments shown in FIG. 15C) so as to generally not interfere with such other resonators located and associated with such other segments, or at least such that any unwanted electromagnetic interference is less than a specified threshold value percentage (e.g., less than 20%, less than 10%, less than 5%, less than 1%, or the like) of the desired interference between the resonators that are co-located within the same segment.

Such phase-control of thermal energy or thermal power delivery can be used by itself, or in combination with one or more of frequency control, duty-cycling, or other techniques described herein, such as to obtained a desired spatiotemporal heating pattern, such as can be suitable for a particular desired application. As explained herein, such phase-control, frequency control, duty-cycling, or combination of the like can use one or more control signals provided by a controller circuit, which can include temperature sensor or one or more other input signals such as to provide closed-loop or other control of the heating delivery techniques described herein. Also, although FIG. 15D illustrates two resonators, e.g., Resonator 1 and Resonator 2, in simplified schematic form for illustrative clarity, these or additional resonators can take on more complex structures, such as that of a meandering or serpentine electrical conductor having a characteristic length, a linear segment having a characteristic length and located closely to another non-parallel, e.g., diverging electrical conductive segment, or other such structures such as described herein, or such as incorporated by reference herein.

Although the above description of phase control has emphasized its application in phase control of power delivery level in certain interfering resonator structures that can be selectively addressed by adjusting a frequency of an electromagnetic input signal such as can be applied to a main line to which the different resonator structures can be coupled, the present techniques of using phase control of power delivery can also be applied to other structures having a lossy dielectric or other active substrate providing a heating location such as can be established or adjusted using a frequency of an applied electromagnetic input signal. For example, Deo U.S. Pat. No. 9,536,758 and Deo U.S. Pat. No. 10,431,478, each of which is incorporated by reference herein in its entirety, show examples of using electrodes having a variable spacing along the length of such electrodes (e.g., a diverging electrode arrangement, a serpentine or meandering electrode arrangement, or the like), such as can be accompanied by a nearby or adjacent semiconductor or other lossy dielectric active substrate. By controlling the relative phase of an electromagnetic signal applied to a first one of the electrodes relative to that of an electromagnetic signal applied to a second one of the electrodes, a power level of thermal energy generated at a heating location in the active substrate can be adjusted, in a similar manner to that described above with respect to the planar resonator examples. By additionally or alternatively adjusting a frequency of the electromagnetic signal applied to the first and second electrodes, the heating location in the active substrate can be moved, such as to different locations along the length of such electrodes, such as described in Deo U.S. Pat. No. 9,536,758 and Deo U.S. Pat. No. 10,431,478.

Material or Environmental Characteristic Sensing Using the Transducers

As explained above, although some description of this document is focused toward a resonator that can be coupled to an output transducer (e.g., an electromagnetic-to-heat transducer, an electromagnetic-to-vibration transducer, an electromagnetic-to-light transducer, or more generally any type of electrically or electromagnetically actuated transducer), the present subject matter can additionally or alternatively include or use such a transducer structure configured as an input transducer (such as a sensor). In physics, when waves flow through different media with different governing characteristics such as, relative permittivity or density, reflection can occur, such that energy transfer to the next medium varies according to the differences in such governing characteristics. Because the present techniques can employ an active substrate or layer, such energy reflection based on such media differences can be detectable such as in the active substrate layer, and can be measured such as by including appropriate embedded sensors and sensor interface circuitry. Therefore, the variations sensed or measured in the active layer can be affected by an indicative of a material characteristic of an environmental layer or region adjacent or near the active substrate. A map of such variations at different locations of the active substrate will correspond to a map of an adjacent or nearby environmental layer or region having varying material characteristics or varying material type. For example, an external environment can be sensed by measuring a differential reflection of the applied AC electromagnetic input signal, or by measuring a transfer of energy of the applied AC electromagnetic input signal between the transducer coupled to the resonator and a surrounding or nearby environment.

For example, in an in vivo catheter application, blood and tissue have different dielectric constants. Blood has a dielectric constant (or relative permittivity ($\epsilon_r$)) of about $\epsilon_r=80$ and tissue has a dielectric constant of about $\epsilon_r=40$. Therefore, between a substrate transducer in a polyurethane catheter having a dielectric constant of about $\epsilon_r=2.2$ and the nearby or surrounding blood or tissue, energy reflection can occur, which can be sensed or measured or mapped, such as to characterize the environment adjacent or nearby or surrounding the transducer. For example, in response to heating provided to the environment via a heating location in an active substrate of the present transducer, a temperature can be sensed or measured at a measurement location at or near the heating location. The resulting sensed or measured temperature can help provide information about one or more of a material type (e.g., blood or tissue) or other material characteristic (e.g., dielectric constant or permittivity ($\epsilon_r$) or the like) of the environment being heated by the transducer. If the nearby or surrounding environment has a material with a larger dielectric constant, such as blood (as opposed to tissue), more electromagnetic energy will be reflected back from the environment toward the active substrate and toward a temperature sensor that can be included and located at or near the transducer, yielding a higher measured temperature by that correspondingly-located temperature sensor. In contrast, if the nearby or surrounding environment has a material with a smaller dielectric constant, such as tissue (as opposed to blood), less electromagnetic energy will be reflected back from the environment toward the active substrate and toward the temperature sensor located at or near the transducer, yielding a lower measured temperature by the temperature sensor. Thus, the measured temperature can be used to compute an indication of a material characteristic (dielectric constant or permittivity) of the material nearby in the environment (and differences in such measured temperatures corresponding to different temperature sensors that are co-located with different transducers can indicate a difference in material characteristics between the different environmental regions near or traversed by those corresponding different transducers). Such indication of the material characteristic can, in turn, be used to classify the material nearby into a material type (e.g., blood vs. tissue, different types of tissue (e.g., bone, fatty tissue, muscle tissue, or the like). If the transducer is placed into a blood vessel, differential temperature measurements along a flow direction can even be used to provide a blood flow measurement as the material characteristic. A lookup table (e.g., generated in advance by testing different known materials) can be used to map the measured temperature to a material characteristic, to a material type, or both. Using multiple temperature sensors, temperatures can be measured at different measurement locations associated with the same or different heating locations, and such different measured temperatures at such different measurement locations can be used to determine a difference in the material characteristic or material type at the different locations.

Figure 16:
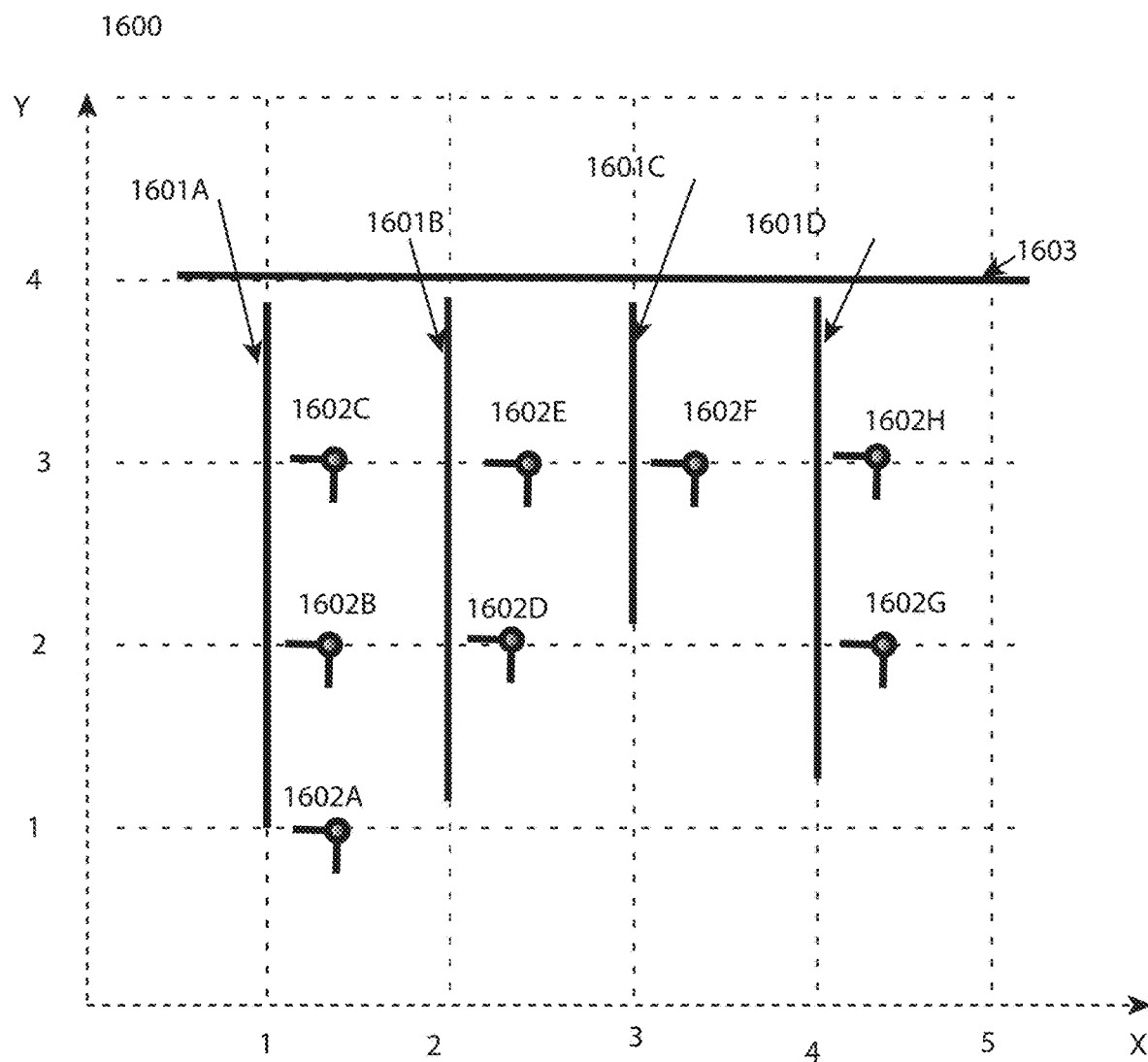
FIG. 16 shows an illustrative example of a heating and sensing transducer arrangement in an X-Y plane.

FIG. 16 shows an illustrative example of a heating and sensing transducer arrangement 1600 in a X-Y plane, however, such X-Y plane can represent an "unrolled" cylindrical surface, such as explained above. The X-Y plane is annotated in FIG. 16 with dashed lines providing a grid to help indicate spatial relationships, however, the arrangement 1600 shown in FIG. 16 is not necessarily drawn to scale. In FIG. 16, resonators 1601 are respectively coupled to a main line 1603 to which an electromagnetic input signal can be delivered at a time-varying addressing frequency, such as to selectively energize a particular one or more of the resonators 1601 that are tuned to that particular addressing frequency, without energizing the other resonators 1601 that are coupled to the main line 1603, but not tuned to the particular addressing frequency being delivered by the electromagnetic input signal on the main line 1603.

In FIG. 16, one or more temperature sensors 1602 can be arranged in correspondence with and physical proximity to corresponding particular resonators 1601, for example, in a manner that allows parasitic capacitive coupling between a particular resonator 1601 and one or more particular temperature sensors 1602, such as without any parasitic coupling of a particular temperature sensor 1602 to other resonators 1601. Thus, energizing a particular resonator 1601 will also energize only those particular temperature sensors 1602 that are associated in correspondence with that particular resonator 1601. For example, the temperature sensors 1602 can include a thermocouple, such as can include dissimilar materials providing a junction across which a voltage signal (indicating temperature) can be measured and read out by sensor interface circuitry, signal filtering or processing circuitry, analog-to-digital converter circuitry, or the like. Thus, a map of measured temperatures at different temperature sensor 1602 measurement locations along a particular resonator 1601 heating location as well as across different resonators 1601 can be created. Such temperature measurements can yield information about a material characteristic of the nearby environment (e.g., dielectric constant), which, in turn can be used to indicate the material type (e.g., blood vs. tissue, bone vs. muscle vs. fat, or the like), such as by comparing the measurement to a previously-generated lookup table mapping the material characteristic to a material type. By placing the apparatus in an environment adjacent to an external calibration material with a known or reference dielectric constant, an indication of dielectric constants of materials can be obtained (this indication can be a relative indication, e.g., to the reference dielectric constant of the external calibration material). Similar to spectrography, one or more thermal peaks from an unknown external material can then be related to a database of thermal peak data corresponding to materials of known dielectrics constants to such as to determine the material type of the unknown external material. Different temperature sensors 1602 associated with the same resonator 1601 can provide differential temperature measurements that can provide an indication of differences in the material characteristic or material type at such different temperature measurement locations, as generally one can assume uniformity of heating being delivered by that same resonator 1601 to the nearby or surrounding environment.

Temperature Profile of Active Substrate Heating Compared to Resistive Heating

Figures 17A, 17B:
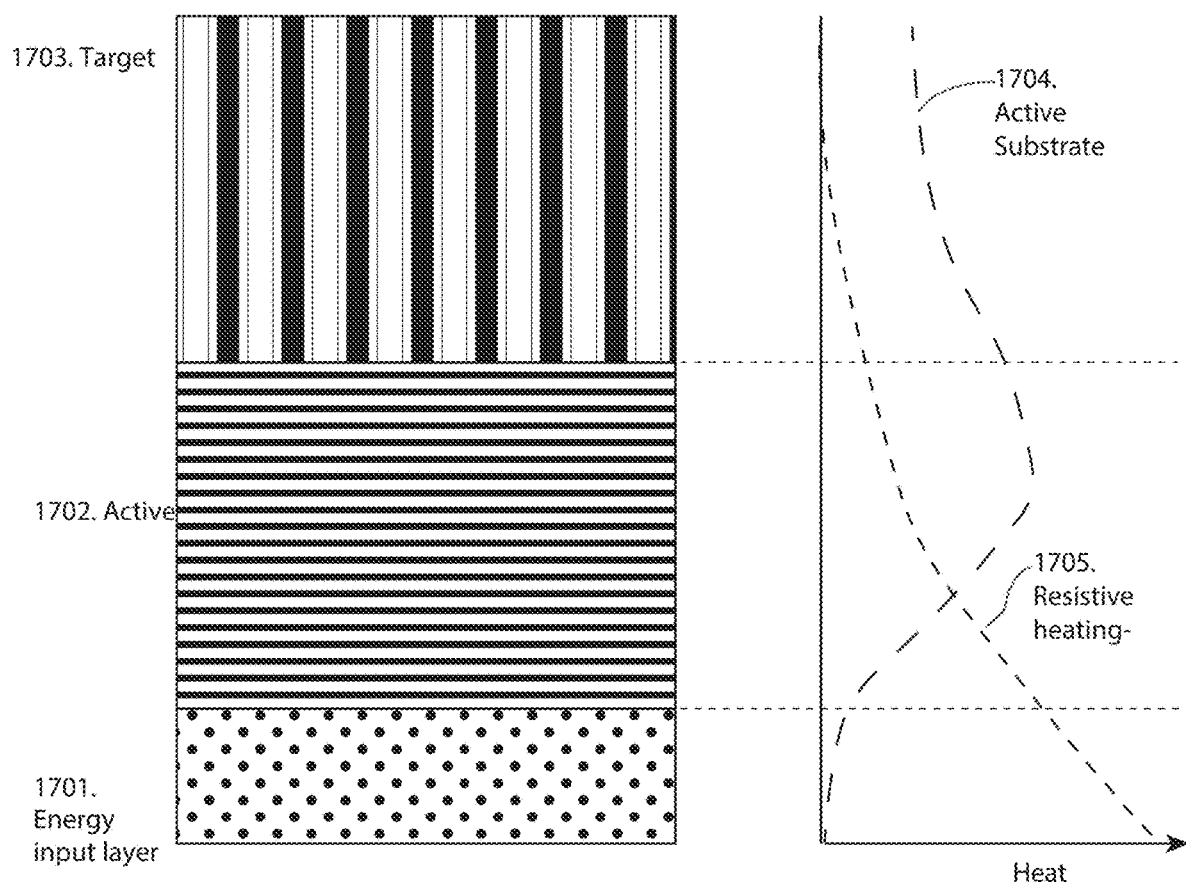
FIG. 17A shows layers including an illustrative example of a cross-sectional arrangement of an energy input layer, an active substrate layer, and a target layer.
FIG. 17B shows a conceptualized position vs. graph, corresponding to the distances shown in FIG. 17A, comparing an active substrate heating temperature profile with a resistive heating temperature profile.

FIG. 17A shows layers including an illustrative example of a cross-sectional arrangement of an energy input layer 1701, an active substrate layer 1702, and a target layer 1703. For example, the energy input layer 1701 can include electrical conductors, such as a planar resonator, diverging or variable distance electrodes, or the like such as described or incorporated by reference herein, such as for receiving a time-varying electromagnetic input signal for activating the active substrate layer 1702 for generating heat in the active substrate layer, which heat can be thermally conducted to the target layer 1703. In an example, the target layer 1703 can include a target region to be heated, such as a target region of a patient that can include blood or tissue, or the target layer 1703 can include a transducer (e.g., optoacoustic, piezoelectric, or the like).

FIG. 17B shows a corresponding conceptualized graph (not real or simulated data, and not drawn to scale) of a temperature profile 1704 such as can be obtained using the active substrate heating techniques described herein, as compared to an approach that uses resistive heating by passing electrical current through the resistance of the electrical conductors in the energy input layer 1701. As shown in FIG. 17B, in a resistive heating approach, the energy input layer 1701 must be resistively heated to a greater temperature to obtain a given level of heating in the target layer 1703, from which the energy input layer 1701 is separated by an intermediate layer 1702. In resistive heating, the energy input layer 1701 may have to be made very hot in order to conduct heat across an intermediate layer, which could possibly damage the intermediate layer. By contrast, by using a time-varying electrical signal in the energy input layer 1701 to energize heat generation in the active substrate layer 1702, more heat can be transferred to the target layer 1705. Also, the present active-substrate heat generation in the active substrate layer 1702 can be better controlled (e.g., dispersed across the volume of the active substrate layer as opposed to being localized in a resistive heating element). This can help keep the temperature within the active region 1702 within a desired temperature range, such as not to exceed a temperature that might damage the material of the active layer 1702.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A transmission line based control device for an integrated transducer, the device comprising:
   a substrate providing or coupled to the transducer; and
   a resonator configured to receive an AC electromagnetic input signal directly, or via an electrically conductive main line coupled with the resonator, wherein the resonator is configured to resonate at its characteristic AC electromagnetic input signal frequency to energize the transducer at a first energy level.

2. The device of claim 1, wherein the resonator is also configured to be off-resonance at a frequency different from its characteristic AC electromagnetic input signal frequency to energize the transducer at a second energy level that is less than the first energy level.

3. The device of claim 1, comprising a plurality of resonators, respectively co-located with corresponding electromagnetic-to-heat transducers, at different locations along the main line, wherein the substrate comprises a lossy dielectric substrate, and wherein:
an individual first one of the resonators is configured to resonate at a first characteristic AC electromagnetic input signal frequency to generate heat in the substrate at the co-located first one of the electromagnetic-to-heat transducers; and
an individual second one of the resonators is configured to be off-resonance at the first characteristic AC electromagnetic input signal frequency, to generate less heat in the substrate at the co-located second one of the electromagnetic-to-heat transducers than is generated in the first one of the electromagnetic-to-heat transducers at the first characteristic AC electromagnetic input signal frequency.

4. The device of claim 1, comprising at least one of:
a tap-line between the resonator and the main line, the tap-line arranged to provide an electrically conductive or inductively-coupled connection between the resonator and the main line; or
a capacitive coupler between the resonator and the main line, the capacitive coupler arranged to provide a capacitively-coupled connection between the resonator and the main line; or
a hybrid coupler between the resonator and the main line, the hybrid coupler arranged to provide, in series, both of: (1) an electrically conductive or inductively-coupled connection between the resonator and the main line; and (2) a capacitively-coupled connection between the resonator and the main line.

5. The device of claim 4, comprising:
a second resonator, arranged in a cascade with the first resonator so as to share at least one of a tap-line, a capacitive coupler, or a hybrid coupler with the first resonator.

6. The device of claim 1, comprising first and second resonators that are configured to be independently addressed using different characteristic AC electromagnetic input signal frequencies.

7. The device of claim 1, comprising a plurality of resonators, wherein respective ones of the resonators are arranged to provide sufficient frequency-domain spacing between corresponding characteristic AC electromagnetic input signal frequencies of corresponding resonators such that ones or groups of the resonators are selectively addressable by applying a variable frequency of the received AC electromagnetic input signal.

8. The device of claim 1, comprising first and second resonators that are configured to electromagnetically interfere with each other to permit phase control of the interfering first and second resonators by specifying or varying a phase of a first electrical signal delivered to the first resonator relative to a phase of a second electrical signal delivered to the second resonator.

9. The device of claim 8, including or coupled to control circuitry configured for selectively addressing the first and second resonators by selecting or varying a frequency of the first electrical signal delivered to the first resonator and a frequency of the second electrical signal delivered to the second resonator, the control circuitry further configured for specifying or varying the phase of a first electrical signal delivered to the first resonator relative to the phase of the second electrical signal delivered to the second resonator.

10. The device of claim 8, wherein the substrate is a lossy dielectric active substrate including or coupled to the first and second resonators, and wherein the control circuitry is configured to control heat generated in the lossy dielectric active substrate including by specifying or varying the phase of a first electrical signal delivered to the first resonator relative to the phase of the second electrical signal delivered to the second resonator.

11. The device of claim 1, comprising:
one or more temperature sensors, configured to measure temperature at a corresponding one or more measurement locations corresponding to one or more respective resonator-activated heating locations of the substrate for communication to a signal processor circuit that is configured to process one or more signals representing measured temperature to compute an indication of a material characteristic of a target region near the one or more measurement locations based on the measured temperature.

12. A method of using a transmission line based control device to control a transducer, the method comprising:
receiving an AC electromagnetic input signal;
using the received AC electromagnetic input signal at a first frequency to resonate a resonator at a characteristic AC electromagnetic input signal frequency to energize a transducer at a first energy level.

13. The method of claim 12, further comprising:
using the received AC electromagnetic input signal at a second frequency to put the resonator off-resonance at a frequency different from the characteristic AC electromagnetic input signal frequency to energize the transducer at a second energy level that is less than the first energy level.

14. The method of claim 13, wherein the energizing the transducer includes at least one of heating or vibrating.

15. The method of claim 12, comprising:
receiving the AC electromagnetic input signal at a first resonator, at its first characteristic AC electromagnetic input signal frequency, to activate a first transducer co-located with the first resonator; and
receiving the AC electromagnetic input signal to be off-resonance at a second resonator, at the first characteristic AC electromagnetic input signal frequency, to activate a second transducer co-located with the second resonator at a level less than that of the first transducer.

16. The method of claim 12, comprising at least one of inductively coupling the received AC electromagnetic input signal to the resonator or capacitively coupling the received AC electromagnetic input signal to the resonator.

17. The method of claim 12, further comprising independently addressing first and second resonators having different characteristic AC electromagnetic input signal frequencies by receiving a variable frequency of the received AC electromagnetic input signal.

18. The method of claim 12, further comprising using phase control of electromagnetically interfering first and second resonators by specifying or varying a phase of a first electrical signal delivered to the first resonator relative to a phase of the second electrical signal delivered to the second resonator.

19. The method of claim 18, wherein a lossy dielectric active substrate provides or is coupled to the first and second resonators, and comprising:
controlling heat generated in the lossy dielectric active substrate including by varying the phase of a first electrical signal delivered to the first resonator relative to the phase of the second electrical signal delivered to the second resonator.

20. The method of claim 12, further comprising:
selectively addressing first and second resonators by selecting or varying a frequency of the first electrical signal delivered to the first resonator and a frequency of the second electrical signal delivered to the second resonator; and
specifying or varying the phase of a first electrical signal delivered to the first resonator relative to the phase of the second electrical signal delivered to the second resonator.

21. The method of claim 12, further comprising:
measuring a temperature at one or more measurement locations corresponding to one or more respective heating locations at which the transducer is energized; and
computing one or more indications of a material characteristic of a target region based on the corresponding measured temperature at the one or more measurement locations.

22. A method of sensing a material characteristic of a target region, the method comprising:
applying a time-varying electromagnetic signal to first and second electrical conductor terminals defining a first layer for electrical conduction in the first layer;
generating heat in an active substrate second layer, adjacent to the first layer, in response to the applying the time-varying electromagnetic signal;
transferring heat from the active substrate second layer to the target region, the target region including a portion that is adjacent to the active substrate second layer;
measuring a temperature at a one or more measurement locations corresponding to the electrical conduction in the first layer; and
computing an indication of the material characteristic of the target region corresponding to the one or more measurement locations based on the measured temperature.

23. The method of claim 22, further comprising computing an indication of material type based on the indication of the material characteristic.

24. An electromagnetic heating sensor apparatus to sense a material characteristic of a target region, the apparatus comprising:
first and second electrical conductor terminals defining a first layer for electrical conduction in the first layer in response to an applied electromagnetic signal; and
an active substrate second layer, adjacent to the first layer, the active substrate second layer configured to generate heat, in response to the applying the electrical signal, at a heating location specified according to a frequency of the applied electromagnetic signal;
one or more temperature sensors, configured to measure temperature at a one or more corresponding measurement locations corresponding to the one or more corresponding heating locations for communication to a signal processor circuit that is configured process a signal representing the measured temperature and compute an indication of the material characteristic of the target region based on the measured temperature.

25. The apparatus of claim 24, further comprising the signal processor circuit, and wherein the signal processor circuit is configured to compute an indication of the material characteristic of the target region and to further compute an indication of material type based on the indication of the material characteristic.

26. A heating method to heat a target region, the method comprising:
applying a time-varying electromagnetic signal to first and second electrical conductor terminals defining a first layer for electrical conduction in the first layer;
generating heat in an active substrate second layer, adjacent to the first layer, in response to the applying the time-varying electromagnetic signal; and
heating the target region, the target region including a portion that is adjacent to the active substrate second layer, wherein the heating creates a temperature profile that is hotter in the active substrate second layer than in the first layer for heating the target region by transferring heat to the target region from the active substrate second layer.

27. An electromagnetic heating apparatus to heat a target region, the apparatus comprising:
first and second electrical conductor terminals defining a first layer for electrical conduction in the first layer in response to an applied electromagnetic signal; and
an active substrate second layer, adjacent to the first layer, the active substrate second layer configured to generate heat, in response to the applying the electrical signal at a heating location specified according to a frequency of the applied electromagnetic signal, the heat generated with a temperature profile that is hotter in the active substrate second layer than in the first layer for heating the target region by transferring heat to the target region from the active substrate second layer.

28. The device of claim 1, wherein the substrate provides the transducer.

29. The device of claim 1, wherein the substrate is coupled to the transducer.

* * * * *